(12) United States Patent
Appelt et al.

(10) Patent No.: US 8,085,144 B2
(45) Date of Patent: Dec. 27, 2011

(54) EQUIPMENT AND METHOD FOR IDENTIFYING, MONITORING AND EVALUATING EQUIPMENT, ENVIRONMENTAL AND PHYSIOLOGICAL CONDITIONS

(75) Inventors: Daren R. Appelt, Austin, TX (US);
Kevin K. Brunson, Aledo, TX (US)

(73) Assignee: Mine Safety Appliances Company, Cranberry Township, PA (US)

( * ) Notice: Subject to any disclaimer, the term of this patent is extended or adjusted under 35 U.S.C. 154(b) by 1373 days.

(21) Appl. No.: 11/346,060

(22) Filed: Feb. 2, 2006

(65) Prior Publication Data
US 2006/0125623 A1 Jun. 15, 2006

Related U.S. Application Data

(63) Continuation-in-part of application No. 10/873,356, filed on Jun. 21, 2004, now abandoned, which is a continuation-in-part of application No. 10/610,013, filed on Jun. 30, 2003, now Pat. No. 6,995,665.

(60) Provisional application No. 60/393,221, filed on Jul. 2, 2002, provisional application No. 60/483,225, filed on Jun. 27, 2003, provisional application No. 60/523,898, filed on Nov. 20, 2003.

(51) Int. Cl.
| | |
|---|---|
| G08B 1/08 | (2006.01) |
| G08B 23/00 | (2006.01) |
| G08B 19/00 | (2006.01) |
| A62B 17/04 | (2006.01) |
| A62B 27/00 | (2006.01) |
| F16K 11/00 | (2006.01) |

(52) U.S. Cl. ............... 340/539.11; 340/573.1; 340/521; 340/526; 128/201.22; 128/202.22; 128/204.23

(58) Field of Classification Search ..................... None
See application file for complete search history.

(56) References Cited

U.S. PATENT DOCUMENTS

| | | | |
|---|---|---|---|
| 3,201,771 A | 8/1965 | Proulx | 340/586 |
| 4,709,202 A | 11/1987 | Koenck et al. | 320/112 |
| 4,727,359 A | 2/1988 | Yuchi et al. | 340/518 |
| 4,996,981 A | 3/1991 | Elenewski et al. | 128/201.15 |
| 5,157,378 A | 10/1992 | Stumberg et al. | 340/521 |
| 5,200,736 A | 4/1993 | Coombs et al. | 340/586 |
| 5,283,549 A | 2/1994 | Mehaffey et al. | 340/521 |
| 5,301,668 A | 4/1994 | Hales | 128/205.23 |
| 5,398,023 A | 3/1995 | Murray | 340/825.44 |
| 5,428,964 A | 7/1995 | Lobdell | 62/176.6 |
| 5,457,284 A * | 10/1995 | Ferguson | 128/201.27 |
| 5,483,229 A | 1/1996 | Tamura et al. | 340/691.7 |
| 5,541,579 A | 7/1996 | Kiernan | 340/573 |
| 5,552,772 A | 9/1996 | Janky et al. | 340/573.1 |
| 5,558,084 A | 9/1996 | Daniell et al. | 128/203.17 |
| 5,635,909 A | 6/1997 | Cole | 340/586 |
| 5,640,148 A | 6/1997 | Lewis et al. | 340/573 |
| 5,659,296 A | 8/1997 | Debe et al. | 340/632 |
| 5,689,234 A | 11/1997 | Stumberg et al. | 340/521 |

(Continued)

*Primary Examiner* — Julie Lieu
(74) *Attorney, Agent, or Firm* — Trop, Pruner & Hu, P.C.

(57) ABSTRACT

A system and method are disclosed for identifying monitoring and evaluating hazardous or potentially hazardous conditions. The system may be worn by safety personnel to detect equipment conditions such as low power supply, environmental conditions such as ambient temperature and/or physiological conditions such as heart rate of a wearer. The system may further include a control unit having electronics operable to communicate signals associated with equipment, environmental and physiological conditions.

31 Claims, 8 Drawing Sheets

U.S. PATENT DOCUMENTS

| | | | |
|---|---|---|---|
| 5,691,707 A | 11/1997 | Smith | 340/682 |
| 5,781,118 A | 7/1998 | Wise et al. | 340/632 |
| 5,917,416 A | 6/1999 | Read | 340/584 |
| 5,973,602 A | 10/1999 | Cole, III et al. | 340/584 |
| 6,057,966 A * | 5/2000 | Carroll et al. | 359/630 |
| 6,075,445 A | 6/2000 | McLoughlin et al. | 340/586 |
| 6,084,522 A | 7/2000 | Addy | 340/630 |
| 6,091,331 A | 7/2000 | Toft et al. | 340/539 |
| 6,118,382 A | 9/2000 | Hibbs et al. | 340/586 |
| 6,199,550 B1 * | 3/2001 | Wiesmann et al. | 128/204.23 |
| 6,417,774 B1 | 7/2002 | Hibbs et al. | 340/584 |
| 6,491,647 B1 * | 12/2002 | Bridger et al. | 600/585 |

* cited by examiner

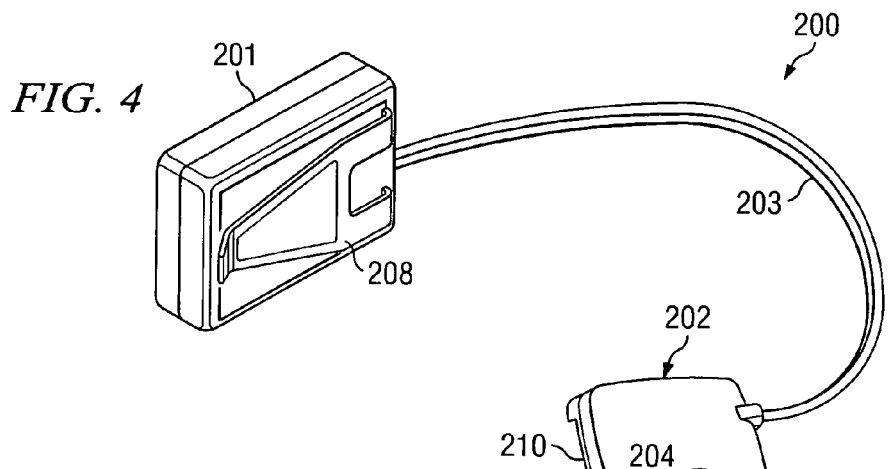
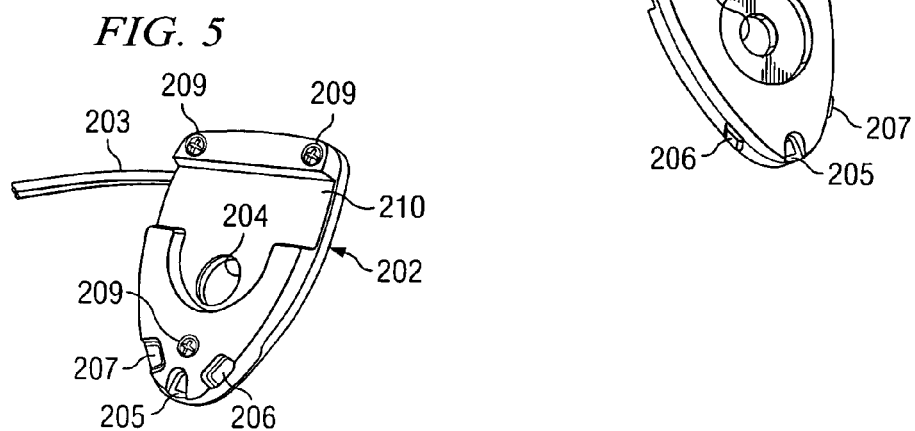
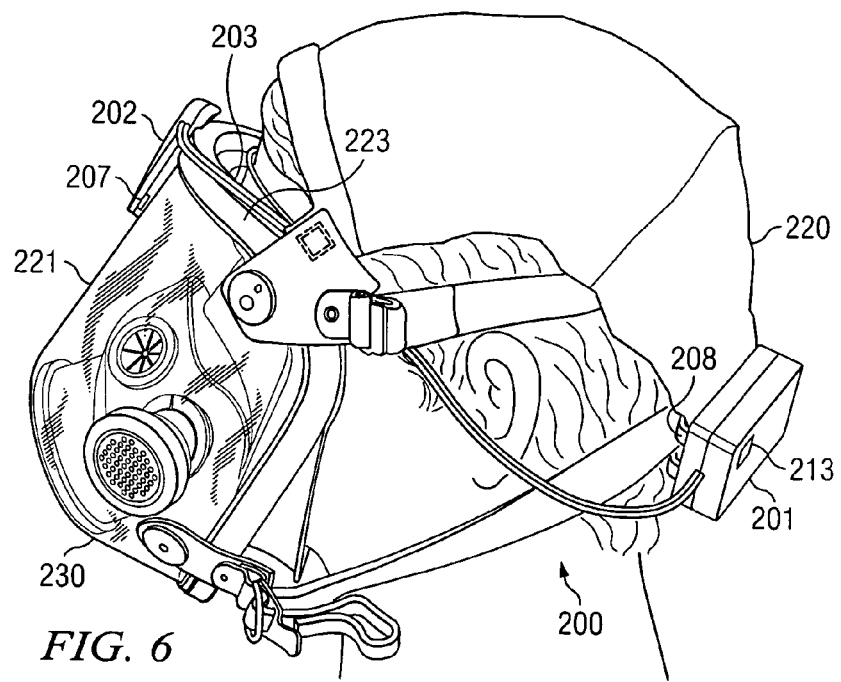

EQUIPMENT AND METHOD FOR IDENTIFYING, MONITORING AND EVALUATING EQUIPMENT, ENVIRONMENTAL AND PHYSIOLOGICAL CONDITIONS

RELATED APPLICATIONS

This application claims priority to and is a Continuation-In-Part of U.S. Continuation-In-Part application Ser. No. 10/610,013, filed Jun. 30, 2003, entitled System and Method for Identifying, Monitoring and Evaluating Equipment, Environmental and Physiological Conditions, which claims priority to U.S. Provisional Application 60/393,221 filed Jul. 2, 2002, now U.S. Pat. No. 6,995,665.

This application claims priority to and is a Continuation-In-Part of U.S. Continuation-In-Part application Ser. No. 10/873,356, filed Jun. 21, 2004, entitled Equipment and Method for Identifying, Monitoring and Evaluating Equipment, Environmental and Physiological Conditions, which claims priority to U.S. Provisional Application 60/483,225 filed Jun. 27, 2003and U.S. Provisional Application 60/523,898 filed Nov. 20, 2003, now abandoned.

TECHNICAL FIELD OF THE DISCLOSURE

The present disclosure relates in general to safety equipment for personnel exposed to hazardous or potentially hazardous conditions and, more particularly, to a system and method for identifying, monitoring and evaluating selected equipment, environmental and physiological conditions.

BACKGROUND OF THE DISCLOSURE

Personnel exposed to hazardous or potentially hazardous conditions typically use a wide variety of protective equipment as appropriate for each respective condition. For example, firefighters, when fighting a fire, generally wear a coat, boots, gloves and other clothing specially created to protect against fire and heat as well as self contained breathing equipment. Although such clothing and equipment provides some protection, firefighter's still face significant dangers including potential flashover. Once ambient temperature in a fire reaches about six hundred degrees Fahrenheit (600 degrees Fahrenheit), the temperature may quickly rise to over eleven hundred degrees Fahrenheit (1100 degrees Fahrenheit). At this point, flashover may occur in which the air ignites and kills or severely injures firefighters. Thus, it is unsafe for personnel to fight fires from within a structure once ambient temperature reaches approximately six hundred degrees Fahrenheit (600 degrees Fahrenheit). In many cases, because they are so well insulated, firefighters do not realize the environment has become dangerously hot.

For other hazardous or potentially hazardous conditions, such as working with explosive, radioactive and/or biologically harmful materials, there are various thresholds and levels beyond which it is unsafe to continue working. Personnel working in hazardous or potentially hazardous conditions must be aware of their respective physiological conditions. An increase in heart rate or problems with breathing may be as hazardous for a firefighter as working in a location with an ambient temperature above six hundred degrees Fahrenheit (600 degrees Fahrenheit).

To alleviate some of the dangers involved in fire fighting, various electronic devices have been developed to provide warnings to firefighters. For example, U.S. Pat. No. 5,640,148 discloses a dual activation alarm system for a personal alert safety system (PASS). U.S. Pat. No. 5,635,909 discloses a temperature monitoring assembly that is incorporated into a garment such as a coat. U.S. Pat. No. 5,541,549 discloses a personal alarm safety system that is designed as part of the firefighter's belt. U.S. Pat. No. 5,137,378 discloses an integrated firefighter safety monitoring and alarm system that provides a number of warnings to a firefighter. This system includes temperature monitoring, an audible alarm and a display to provide additional information including a visible warning.

A wide variety of detectors, sensors and monitors are commercially available to warn personnel about potentially explosive mixtures, increased radiation levels above normal background and the presence of biological hazards. Such detectors, sensors and monitors may be installed at fixed locations, hand held or attached to clothing and other safety equipment associated with personnel working in hazardous or potentially hazardous conditions.

Even with such conventional devices, firefighters are still injured or killed by flashovers and workers are injured or killed by industrial explosions. The complexity of conventional devices, the difficulties of fire fighting environments and the type and location of the warnings often cause firefighters not to hear audible warnings or not to see visible warnings of dangerous ambient temperatures. It is often even more difficult for workers to recognize and take appropriate action when exposed to hazardous or potentially hazardous explosive, radioactive and/or biologically harmful conditions.

Prior temperature sensors and detectors associated with fire fighting equipment generally do not provide confirmation of satisfactory temperature measurements at a field location. Calibration at a testing facility or laboratory is often the only way to confirm satisfactory temperature measurements by most conventional temperature sensors and detectors.

SUMMARY OF THE DISCLOSURE

In accordance with teachings of the present disclosure, a system and method are provided to identify, monitor and evaluate environmental and physiological conditions. One embodiment of the present disclosure includes a personal situation awareness device which may be used by a person exposed to hazardous or potentially hazardous conditions. Such personal situation awareness devices may be worn by first responders to terrorists acts, particularly biological and chemical attacks or radiological attacks such as a "dirty" bomb.

Personal situation awareness devices incorporating teachings of the present disclosure may be used to identify and monitor variable relationships between environmental conditions exterior to a person's safety equipment, environmental conditions within an interior of the safety equipment and/or the safety equipment itself and associated physiological condition effects of combined environmental and physiological conditions on the respective person. Identifying, monitoring and evaluating exterior environmental conditions, interior environmental conditions and associated physiological effects may substantially reduce the number of injuries and/or deaths from working with hazardous or potentially hazardous conditions. For some applications such as firefighting, measuring environmental and physiological conditions at a facemask may be critical for survival.

The present disclosure allows design, development and manufacture of personal situation awareness devices which may be used to prevent injury and/or death of personnel working in hazardous or potentially hazardous conditions.

Personal situation awareness devices incorporating teachings of the present disclosure may be used to identify, monitor and evaluate physiological conditions of a wearer. Such personal situation awareness devices may also monitor variable relationships between environmental conditions and physiological conditions of the wearer. Such personal situation awareness devices may be used to collect data, interpret data and communicate with other individual wearers and/or with one or more remote locations. Such devices may analyze data and initiate appropriate alerts and warnings.

Another aspect of the present disclosure may include connecting sensors, displays and power sources that may be part of an SCBA system or other safety equipment associated with a person wearing the safety system. By sharing sensors, displays and power sources with other elements, an entire ensemble worn by the person may be manufactured more efficiently and provide increased service life, safety and reliability.

The system may include a control unit operable to be coupled to safety equipment or to a person working in a hazardous or potentially hazardous condition. The control unit may have electronics operable to communicate data associated with environmental and physiological conditions. For one application the system may include a sensor unit or a sensor assembly operable to be positioned in an ambient environment and coupled with a facemask. For other applications a sensor unit may be positioned at optimum locations or associated safety equipment. The sensor unit or sensor assembly may include one or more sensors having an operating mode dependent upon the presence of one or more hazardous or potentially hazardous conditions. The sensor unit or sensor assembly may be communicatively coupled to the control unit.

All components shown in FIGS. 1, 3, 10B, 12 and 14 may be integrated into a facemask where the display features could simulate dangerous training scenarios.

For some applications, a safety system may be designed in accordance with teachings of the present disclosure for use in a training environment. For other applications, a safety system may be designed in accordance with teachings of the present disclosure for use in hazardous environments such as major building fires. Systems designed for use in a training environment may provide substantial quantities of information to a person wearing the safety system. Systems designed for use in hazardous environments such as building fires may provide more limited information to prevent overloading the wearer. For example, the signals provided to a wearer working in a potentially hazardous environment may be limited to:
1. Safe;
2. Continue working;
3. Increasing potential danger;
4. Decreasing potential danger; and
5. Leave immediately.

A wide variety of sensors may be imbedded in a facemask or other portions of safety equipment in accordance with teachings of the present disclosure. Multiple layers of polyester film may be used to install sensors and other components within a facemask, a helmet, a jacket, a vest, and/or gloves which are worn by a wearer exposed to hazardous or potentially hazardous conditions.

A laminated facemask and face shields may be formed from polycarbonate materials and polyester materials in accordance with teachings of the present disclosure. Printed circuits, sensors and other electronic devises may be imbedded within a facemask or other pieces of safety equipment in accordance with teachings of the present disclosure.

A safety system formed in accordance with teachings of the present disclosure may include multiple transmitters and multiple receivers to establish communication links between command and control station, other personnel wearing compatible safety equipment, two or more pieces of safety equipment associated with each wearer, and a remote data base or remote information storage unit. For some applications, wireless communication techniques such as "WiFi" may be used to provide desired communication links.

Measuring environmental and other parameters at a firefighter's face piece is vitally important. Since air flow for breathing is often the most vital resource when exposed to a hazardous environment, a face piece is frequently the most vital piece of equipment. Monitoring conditions at the face piece is the most effective way to protect a worker in a hazardous environment.

By measuring at the face piece, it is possible to monitor nearly all of the critical parameters that might affect safety. For example, the following information may be measured, displayed, and communicated via the face piece:
environmental temperature
equipment temperature
explosive gasses
poisonous gasses
biohazards
radionuclides
air supply temperature
air supply flow rate
body temperature
heart rate
breathing rate
infrared vision
precision location
communication Measurements may often be made at a face piece to provide the best overall information for the safety of workers in hazardous environments. Frequently, no other point of measurement allows the same level of protections.

A face piece with fully integrated instrumentation formed in accordance with teachings of the present disclosure protects workers exposed to hazardous or potentially hazardous conditions.

Technical benefits of the present disclosure includes a new and unique method of upgrading existing SCBA facemasks with the above referenced features. By integrating one or more of these features entirely within the facemask lens, a standard lens in a SCBA system may be replaced by a high-tech lens. Features of the present disclosure may be easily integrated into existing SCBA products. It may be easier for SCBA manufacturers to qualify an alternate lens with regulatory agencies as compared to qualify an accessory component having these same features.

One aspect of the present disclosure includes a "smart lens" that replaces a standard lens to convert a normal SCBA facemask into a "smart mask". Another aspect of the present disclosure includes using a firefighter's walkie-talkie as a relay to communicate data from a safety system incorporating teachings of the present disclosure.

Various features of the present disclosure may be included a product family of safety equipment and clothing satisfactory for use hazardous materials. The product family may include bio-sensors, radiation sensors, and gas analyzer sensors, infrared sensors, etc.

Additional features and benefits of the present disclosure include, but are not limited to:

- Record data for after action analysis and training. Change behavior of first responders.
- Dual temperature sensors to measure heat flux.
- Provide "System Bus" to allow adding "modules" and removing "modules" as required for each situation.
- Complete system in a facemask may replace existing facemasks.
- Single, integrated unit in a facemask.
- RFID links with associated equipment.
- Wireless transceivers.
- Microproximity sensors.
- Count heat cycles. Count equipment cycles. Record high temperature and low temperature outside normal operating limits. Estimate remaining service life of equipment. Establish required maintenance periods for equipment. Predict equipment failure and remove personnel from hazardous location.
- RFID and wireless communication allows effective monitoring of each piece of equipment associated with a person working in a hazardous location.

BRIEF DESCRIPTION OF THE DRAWINGS

A more complete understanding of the present disclosure and advantages thereof may be acquired by referring to the following description taken in conjunction with accompanying drawings in which like reference numbers indicate like features and wherein:

FIG. 4 is a schematic drawing showing an isometric view of a system operable to identify, monitor, evaluate and alert safety personnel of hazardous or potentially hazardous conditions in accordance with teachings of the present disclosure;

FIG. 5 is a schematic drawing showing a rear perspective view of the sensor assembly in FIG. 4 incorporating teachings of the present disclosure;

FIG. 6 is a schematic drawing showing a perspective, side view of the system of FIG. 4 coupled to a facemask according to one embodiment of the present disclosure;

DETAILED DESCRIPTION OF THE DISCLOSURE

Figure 1:
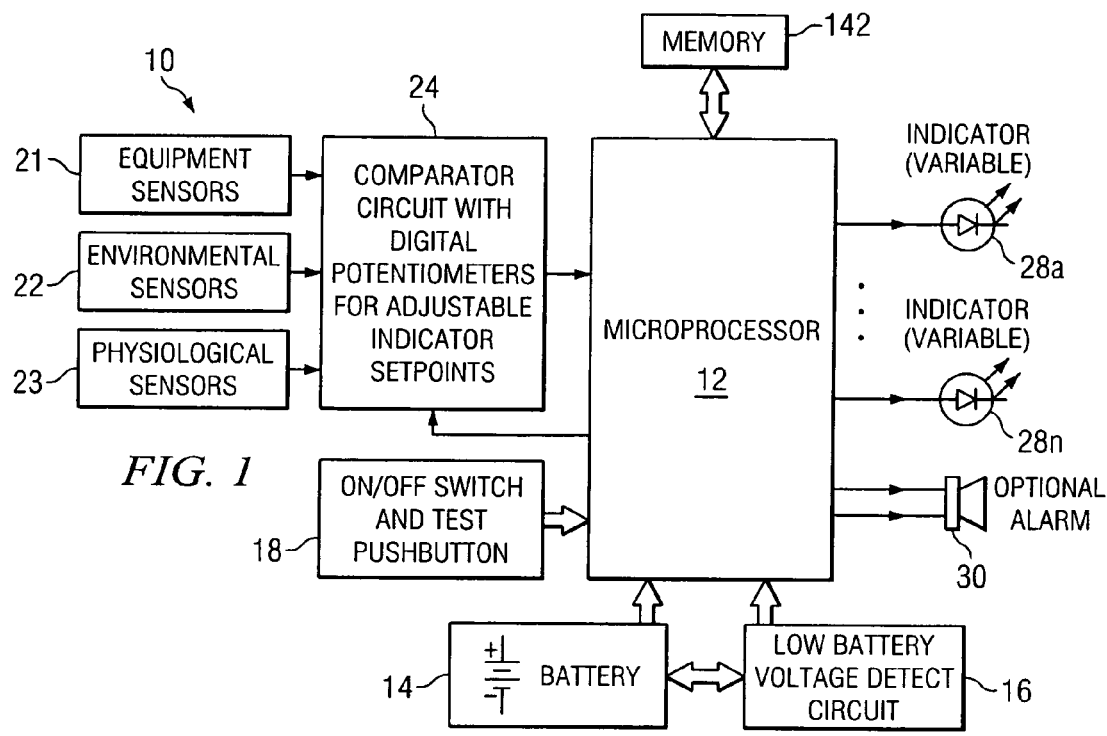
FIG. 1 is a block diagram of one embodiment of a system operable to identify, monitor, evaluate and alert personnel of hazardous or potentially hazardous conditions in accordance with teachings of the present disclosure.

Preferred embodiments of the present disclosure and its advantages are best understood by referring to FIGS. 1-15C of the drawings, in which like numbers reference like parts.

The terms "safety equipment" and "protective equipment" are used throughout this application to include any type of clothing such as a coat, vest, hat, apron, boots and/or gloves which may be used to protect a wearer from hazardous or potentially hazardous environments. The terms "protective equipment" and "safety equipment" may also include helmets, visors, hoods, facemasks, oxygen tanks, air bottles, self-contained breathing apparatus (SCBA), chemical suits and any other type of clothing or device which may be worn by a person to protect against fire, extreme temperatures, reduced oxygen levels, explosions, reduced atmospheric pressure, radioactive and/or biologically harmful materials.

The term "environmental conditions" is used throughout the application to include both external environmental conditions (ambient air temperature, wind conditions, barometric pressure, gas concentrations, oxygen levels, etc.) and internal environmental conditions (temperature of safety equipment, air temperature and pressure within a biological or chemical clean up suit, gas concentrations within a biological or chemical clean up suit, etc.). Environmental conditions may include the operating condition of safety equipment and the results of using such safety equipment such as air capacity and flow rates to a person wearing an SCBA.

The term "facemask" as used in this application may also comprise a face piece, lens or any protective covering of a wearer's face satisfactory for use in a hazardous or potentially hazardous condition.

The term "hazardous or potentially hazardous conditions" is used throughout this application to include environmental conditions such as high ambient temperature, lack of oxygen, and/or the presence of explosive, exposure to radioactive or biologically harmful materials and exposure to other hazardous substances. Examples of hazardous or potentially hazardous conditions include, but are not limited to, fire fighting, biological and chemical contamination clean-ups, explosive material handling, working with radioactive materials and working in confined spaces with limited or no ventilation. The term "hazardous or potentially hazardous conditions" may also be used throughout this application to refer to physiological conditions associated with a person's heart rate, respiration rate, core body temperature or any other condition which may result in injury and/or death of an individual. Depending upon the type of safety equipment, environmental conditions and physiological conditions, corresponding thresholds or levels may be established to help define potential hazardous conditions, hazardous conditions and critical conditions.

Permissible exposure limits (PELs) have been established by the U.S. Department of Labor Occupational Safety & Health Administration (OSHA) to protect workers against the effects of exposure to various hazardous or potentially hazardous materials and substances. PELs are frequently associated with air quality standards. Threshold limit values (TLVs) have been established by the American Conference of Governmental Industrial Hygienists to help establish safe working environments when exposed to various hazardous or potentially hazardous materials and substances. Both PELs and TLVs may be used to define one or more critical conditions and an acceptable length of time, if applicable, for exposure to each critical condition. Workplace environmental exposure limits (WEELs), recommended exposure limits (RELs) and industry developed occupational exposure limits (OELs) may also be used to establish one or more critical conditions and acceptable length of time, if applicable, for exposure to each critical condition.

A data base with appropriate PELs, TLVs, WEELs, RELs and OELs may be stored within memory 142 or data storage 542a. See FIGS. 1, 2, and 14. Also, an appropriate data base with this same information may be stored at a remote facility such as remote data storage 542b and communicated with safety system 500 through an appropriate communication link. See FIG. 14.

The term "critical condition" is used throughout this application to define a hazardous or potentially hazardous condition which may result in injury or loss of life. A critical conditional may be a hazardous or potentially hazardous environmental condition. A critical condition may also be a hazardous or potentially hazardous physiological condition or a combination of environmental and physiological conditions including the rate of change of such conditions. Depending upon the type of safety equipment, environmental conditions and physiological conditions, corresponding thresholds or levels may be established to help define potential hazardous conditions, hazardous conditions and critical conditions.

The term "critical data" is used throughout this application to include any information or data which indicates the presence of a hazardous or potentially hazardous condition or the presence of a critical condition. The rate of change of environmental conditions and/or physiological conditions may be "critical data".

FIG. 1 is a block diagram of one embodiment of a system, indicated generally at 10, operable to identify, monitor, evaluate and alert personnel of hazardous or potentially hazardous conditions according to teachings of the present disclosure. System 10 may include microprocessor 12 which receives power from battery 14. Microprocessor 12 may serve as a control unit for system 10. However, a wide variety of other control units such as digital signal processors and general purpose microprocessors or microcontrollers may also be satisfactorily used.

Battery 14 may be replaced by a user and may be conserved by switching system 10 off when not in use. System 10 may also include a low battery voltage detection circuit 16 and may be turned on and off by combined on/off switch and test button 18. Switch 18 may be backed up by an automatic switch (not expressly shown) that turns system 10 on when a hazardous or potentially hazardous condition reaches a selected set point, such as ambient temperature greater than one hundred fifty degrees Fahrenheit (150° F.) or heart rate greater than one hundred twenty (120) beats per minute.

Equipment sensors 21 may be used to monitor and measure data related to equipment temperature, air supply temperature and/or pressure, air flow rates, battery power levels, status of communication links and/or any other data required to monitor and evaluate satisfactory performance of any equipment associated with a person wearing system 10. Environmental sensors 22 may be used to detect, identify and measure a variety of environmental conditions such as ambient air temperature, explosive gas concentrations, biological agent concentrations, radioactivity levels associated with one or more radionuclides and/or any other hazardous or potentially hazardous environmental condition. For some applications equipment sensors 21 may be included as part of environmental sensors 22. Physiological sensors 23 may be used to monitor various physiological conditions such as respiration rate, blood oxygen level, core body temperature, heart rate and/or any other physiological condition required to identify, monitor and evaluate the physiological condition of a person wearing system 10. Equipment sensor 21 and/or physiological sensor 23 may also be used to measure movement or lack of movement by a wearer and/or equipment associated with the wearer. For some applications, a global positioning system or other location sensor (not expressly shown) may be coupled with microprocessor 12 and/or comparator circuit 24.

For some applications equipment sensors 21, environmental sensors 22 and physiological sensors 23 may include digital potentiometers (not expressly shown) which may be used to provide adjustable set points to indicate the presence of one or more hazardous or potentially hazardous conditions and one or more critical conditions. Environmental sensors 22 may include a resistive temperature device (RTD), thermocouple, thermistor, infrared (IR) sensor, pressure detector, gas detector, radiation detector, biohazard detector, video camera or any other environmental detector. System 10 may have multiple thresholds or set points corresponding with different levels for potentially hazardous conditions, hazardous conditions and critical conditions. Additional thresholds or set points may be implemented by system 10 when appropriate. Also, one or more set points may be set or modified by signals from microprocessor 12.

In operation, comparator circuit 24 provides a signal to microprocessor 12 in response to a comparison between respective set points and respective outputs from equipment sensors 21, environmental sensors 22 and physiological sensors 23. Microprocessor 12 may then provide signals to drive or actuate one or more visible indicators 28a through 28n. Various types of light emitting diodes (LED), liquid crystal displays (LCD), portions of a heads-up-display, fiber optic indicators or incandescent indicators may be used as visible indicators 28a through 28n. For one embodiment, visible indicators 28a through 28n may indicate ambient temperatures of 300 degrees Fahrenheit and 600 degrees Fahrenheit and heart rates of 120 beats per minute and 150 beats per minute. However, these set points are preferably variable and may have other values. Microprocessor 12 may provide signals to an optional alarm 30. Alarm 30 may, for example, be an audible or vibration alarm. Visual indicators 28a-28n may be green and red indicators such as light emitting diodes (LEDs) or miniature incandescent lights. Visual indicators 28a-28n may be mounted within the peripheral vision of a person wearing a facemask, helmet, self-contained breathing apparatus (SCBA) or other protective equipment. Visual indicators 28a-28n may be set to glow when an environmental and/or physiological condition reaches a respective set point. Early signaling will afford personnel wearing system 10 with ample time to react to the corresponding critical condition and make informed decisions as to whether to proceed or withdraw. Not only will the present disclosure save many lives, but, in turn, will also save money that would otherwise be spent on treatment of injured personnel and/or replacing damaged safety equipment and associated downtime costs.

Microprocessor 12 may provide additional enhancements to identify, monitor, evaluate and alert a wearer of hazardous or potentially hazardous conditions. For example, system 10 may use time averaged measurements for additional or alternate indicators. Such time averaged measurements are helpful to identify when a wearer has been exposed to a hazardous or potentially hazardous condition for a given amount of time. With respect to fire fighting such time averaged measurements may include: 160 degrees Fahrenheit for sixty seconds, 180 degrees Fahrenheit for thirty seconds, 212 degrees Fahrenheit for fifteen seconds, and 500 degrees Fahrenheit for ten seconds. System 10 may react to such events by providing additional visible indicators and/or alarms. Sensors 21, 22, and 23 along with comparator 24 and microprocessor 12 provide substantial flexibility in programming system 10 for a wide variety of hazardous or potentially hazardous conditions with appropriate set points selected for each critical condition.

System 10 may record an exposure history for post-event analysis and for training personnel. For example, ambient air temperature in a fire fighting environment may be recorded at specified time intervals to give firefighters or other safety personnel an idea of temperature profiles during training or while working within a structure fire or other hazardous site. System 10 may include global positions system (GPS) devices or other equipment to determine location and "map" temperature gradients or other potentially hazardous conditions within a site. Recorded data may be placed in an on-board random access memory (not expressly shown) or other digital data recorder. Recorded data, including position information, may be used to improve supervision of firefighters and other safety personnel and to provide better training for such personnel. System 10 allows better standardization of policies, practices and procedures with respect to personnel working in hazardous or potentially hazardous conditions.

Figure 2:
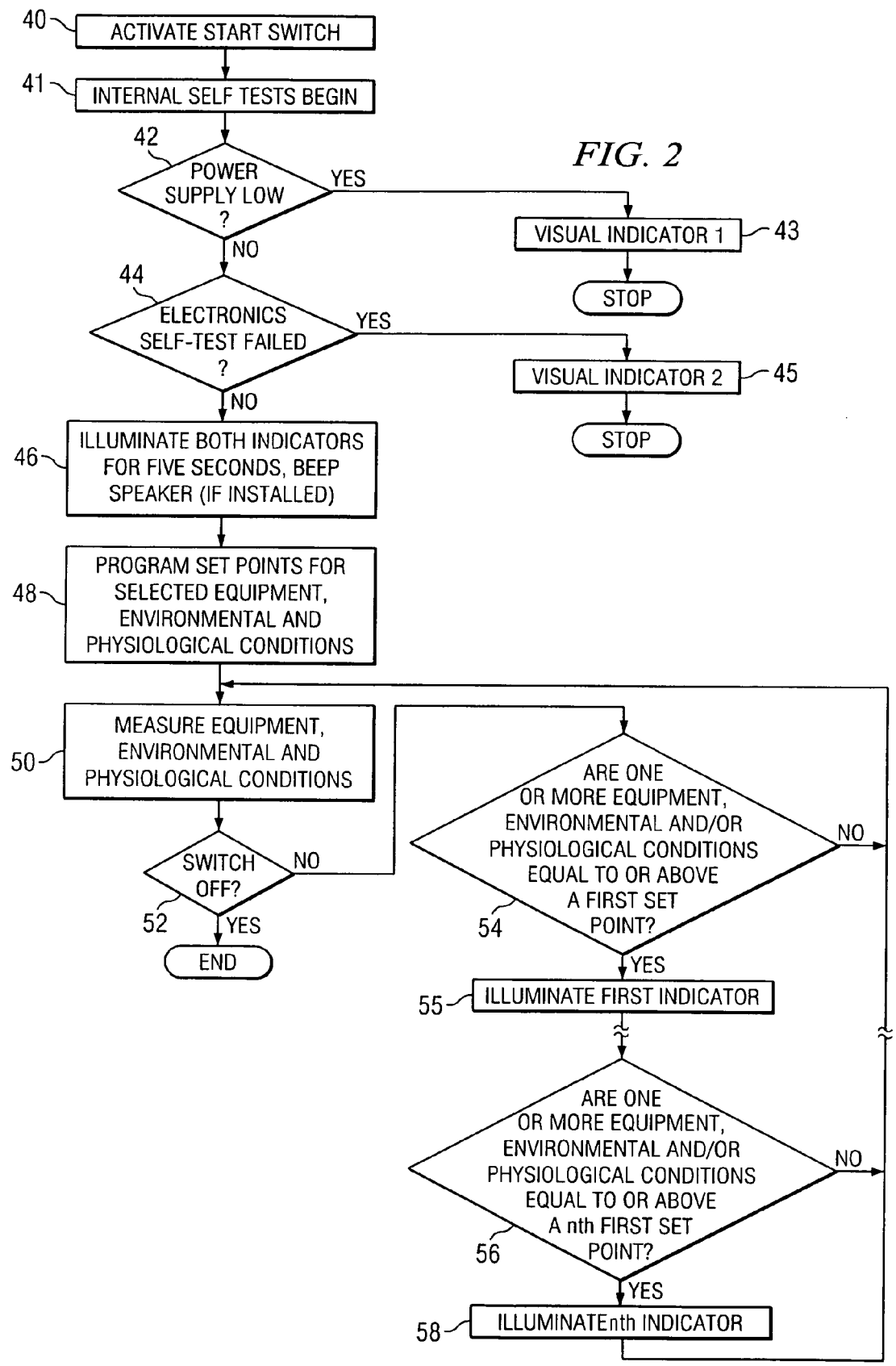
FIG. 2 is a flow chart of one embodiment of a method to identify, monitor, evaluate and alert personnel of hazardous or potentially hazardous conditions in accordance with teachings of the present disclosure.
Figure 7:
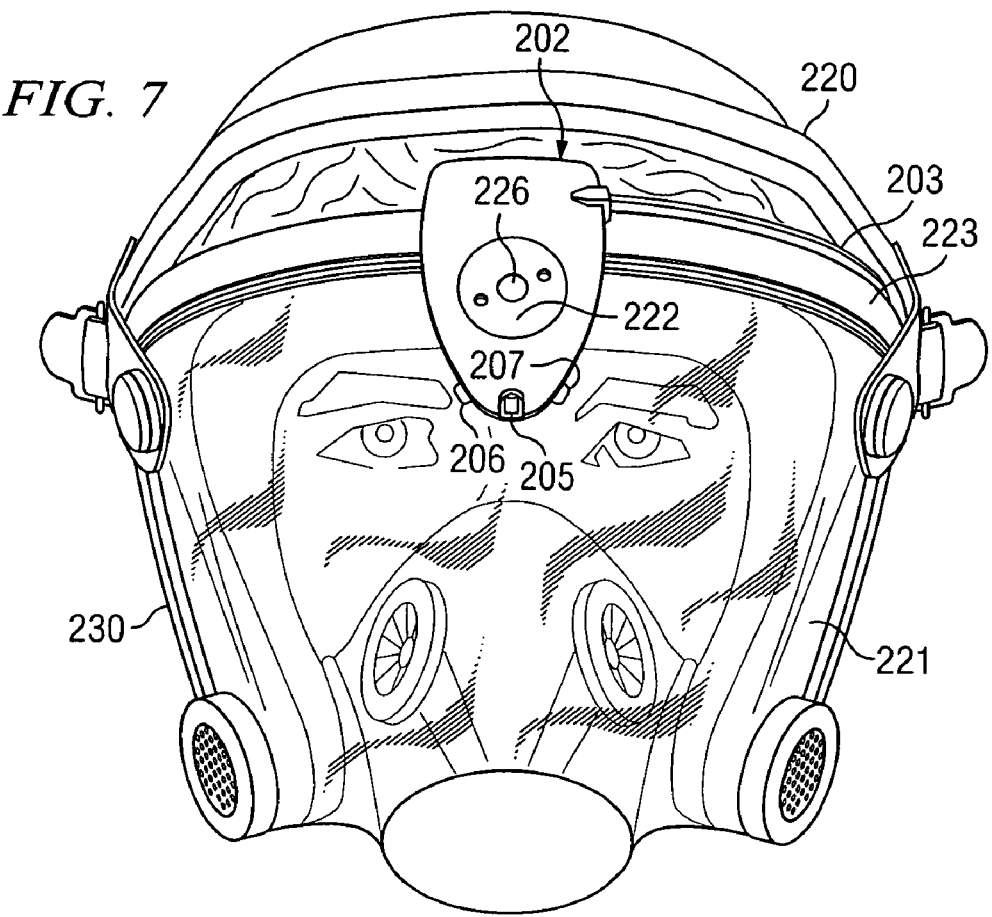
FIG. 7 is a schematic drawing in elevation showing a front view of the system and facemask of FIG. 4.

FIG. 2 is a flow chart of one embodiment of a method for alerting safety personnel of hazardous or potentially hazardous conditions according to the present disclosure. As shown, at step 40, a start switch may be activated. This activation may be manual or automatic. At step 41, a system incorporating teachings of the present disclosure may begin an internal self test. At step 42, the system checks whether the battery or other power supply is low. If so, at step 43, the system flashes one or more visual indicators to signal the problem. At step 44, the system determines whether the self-test failed. If so, at step 45, the system flashes one or more visual indicators to signal this failure. If the test did not fail, at step 46, the system may illuminate one or more visual indicators for five seconds and beep on a speaker (if any) or activate a vibrator (if any).

At step 48, the system may allow a wearer to program set points for respective equipment, environmental and physiological conditions. For some applications the set points may already be established. At step 50, the system measures selected equipment, environmental and physiological conditions using associated equipment sensors, environmental sensors and physiological sensors. At step 52, the system determines if it is switched off. If so, then the process stops. Otherwise, the system checks, at step 54, whether one of the equipment, environmental or physiological conditions is at a first set point (e.g., ambient air temperature 300 degrees Fahrenheit, 120 heart beats per minute, air supply temperature 100 degrees Fahrenheit) or greater. If not, then the system returns to measuring selected equipment, environmental and physiological conditions. If one of the equipment, environmental or physiological conditions is greater than the first set point, the system may illuminates one or more visual indicators in step 55. At step 56, the system may check whether the equipment, environmental or physiological condition is greater than a second set point (e.g., ambient air temperature 600 degrees Fahrenheit, 140 heart beats per minute or air supply temperature 110 degrees Fahrenheit). If not, the system returns to measuring selected equipment, environmental and/or physiological conditions of step 50.

If the equipment, environmental or physiological condition is greater than the second set point, the system may illuminate one or more visual indicators in step 58 and then return to measure selected equipment, environmental and physiological conditions. In this manner, the system continually monitors selected equipment, environmental and physiological conditions and provides visible warning of any equipment, environmental and physiological condition which is above the respect first or second set point.

Other embodiments of the present disclosure may include other steps. For example, another embodiment may include time averaged measurements for averaging equipment, environmental and physiological conditions over a specified interval of time and alerting a person wearing the system when a hazardous or potentially hazardous condition is present.

Visible indicators may be placed in the field of view, for example, while a firefighter is fighting a fire. When at least one equipment, environmental or physiological condition reaches a first set point (e.g., ambient temperature 300 degrees Fahrenheit, 130 heart beats per minute, air supply temperature 100 degrees Fahrenheit), a first indicator may be illuminated and stay on as long as the condition is at the first set point or above. When the condition reaches a second set point (e.g., ambient temperature 600 degrees Fahrenheit or 150 heart beats per minute, air supply temperature 120 degrees Fahrenheit), the second indicator may be illuminated and stay on as long as the condition is at the second set point or above. The second indicator may indicate that there is a very short time period before the equipment, environmental or physiological condition reaches a critical condition. The person wearing the system should consider immediately leaving the area to avoid a life threatening situation when the second indicator is illuminated.

The first set point may be preset at a manufacturer's suggested level for normal functioning of associated safety equipment to serve as an indicator of satisfactory equipment operation. The second set point may be selected to indicate a critical condition such as equipment failure or personal injury. As mentioned above, equipment, environmental and physiological set points may be varied by reprogramming comparator circuit 24 and/or microprocessor 12 to provide alerts for any critical condition.

Figure 3:
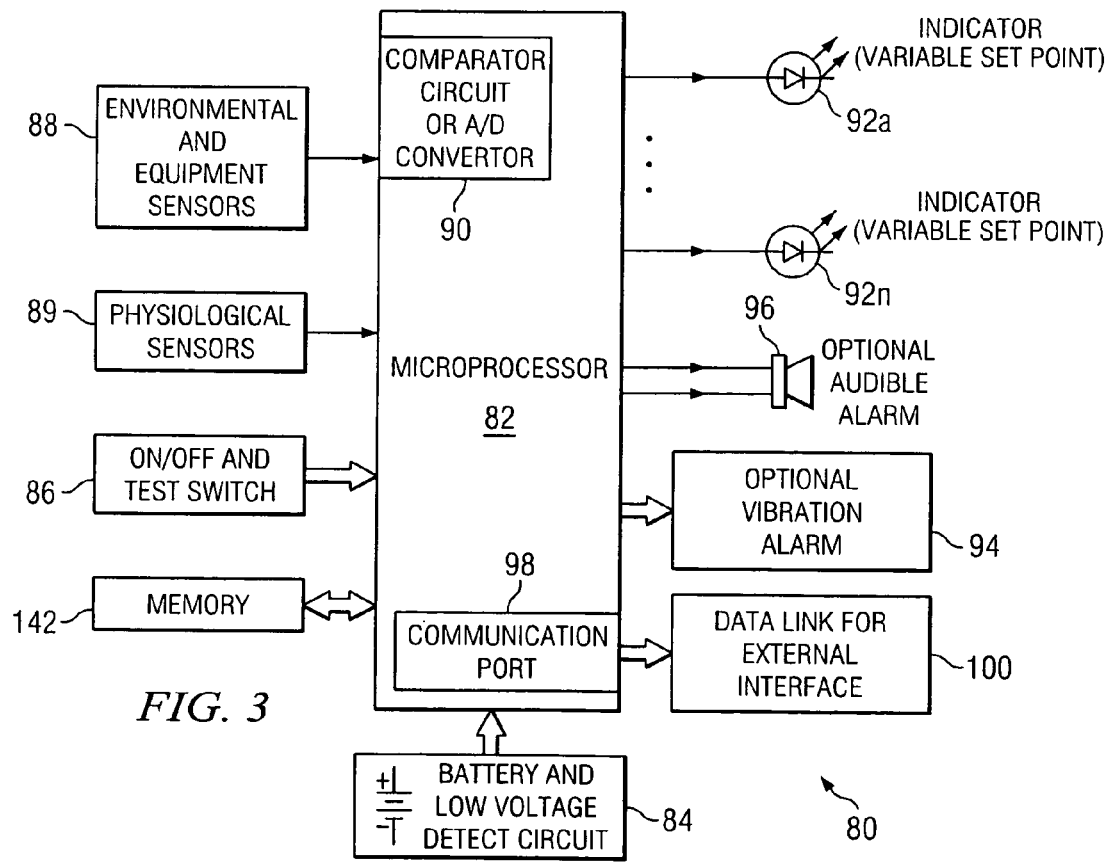
FIG. 3 is a block diagram of another embodiment of a system operable to identify, monitor, evaluate and alert personnel of hazardous or potentially hazardous conditions in accordance with teachings of the present disclosure.

FIG. 3 is a block diagram of system 80 operable to alert a person wearing this system of hazardous or potentially hazardous conditions in accordance with teachings of the present disclosure. For the embodiment of FIG. 3, system 80 includes microprocessor 82 that receives power from battery and low voltage detection circuit 84. Power supplies (not expressly shown) other than a battery may be used with system 80. Microprocessor 82 serves as a control unit for system 80. Alternative types of control devices such as digital signal processors may be used as the control unit. System 80 may be turned on and off by an on/off and test switch 86 which also may operate as a push-button for some applications.

Combined environmental and equipment sensor unit 88 may be used to monitor various ambient conditions and conditions of safety equipment associated with a person wearing system 80. Physiological sensor unit 89 preferably monitors one or more physiological conditions of the person wearing system 80. Environmental and equipment sensor unit 88 and physiological sensor unit 89 may provide outputs to comparator circuit 90 of microprocessor 82. Microprocessor 82 then provides signals to visible indicators 92a through 92n with variable set points to indicate selected equipment, environmental and physiological conditions.

In operation, comparator circuit 90 may provide a signal to microprocessor 82 in response to signals from environmental and equipment sensor unit 88 and physiological sensor unit 89. Microprocessor 82 then provides signals to drive or actuate visible indicators 92a-92n. Further microprocessor 82 may provide signals to an optional vibration alarm 94 (e.g., mechanical motor, solenoid) and audible alarm 96. Further, microprocessor 82 comprises communication port 98 which may output data to data link port 100 coupled with one or more external interfaces. Data link port 100 may be used, for example, to recover a recorded ambient temperature history or heart rate history or other selected equipment, environmental or physiological information.

Systems 10 and 80 formed in accordance with teachings of the present disclosure may include software applications and appropriate data bases or other information required to evaluate data associated with one or more critical conditions to determine when action should be taken to prevent injury and/or death to an individual working with a critical condition. System 10 and 80 may be used to identify, monitor and evaluate physiological conditions of a person working in a hazardous or potentially hazardous environment including location and movement or lack of movement of the person. Systems 10 and 80 may be used to identify, monitor and evaluate external environmental conditions and internal environmental conditions.

FIGS. 4, 5, 6 and 7 show one example of a system for alerting personnel of hazardous or potentially hazardous conditions in accordance with teachings of the present disclosure. System 200 may be easily coupled or removed from safety equipment. System 200 includes sensor unit or sensor assembly 202 having aperture 204 and mounting channel 210 for mounting sensor assembly 202 to safety equipment such as a safety helmet, face shield or facemask. Sensor assembly 202 further includes first indicator 206, second indicator 207 and one or more sensors 205 operable to identify and detect environmental conditions such as ambient temperature. Sensor assembly 202 may include waterproofing such as a high-temperature clear silicone plastic potting compound operable to withstand elevated temperatures while limiting exposure to water and other elements which may be encountered by a person wearing system 200. For some applications sensors 205 may be operable to detect explosive gas mixtures or radiation.

Sensor assembly 202 may be coupled via cable 203 to housing 201 which includes one or more control units, associated electronics and software applications to identify, monitor, evaluate and/or alert safety personnel of hazardous or potentially hazardous conditions. See FIGS. 1, 2 and 3. Housing 201 may include clip 208 operable to be attached to safety equipment such as a helmet, protective clothing, facemask webbing and the like. In one embodiment, housing 201 may be made of a waterproof material operable to withstand high temperatures while minimizing undesired exposure of electronic circuits stored within housing 201. Housing 201 may include high-temperature silicon-rubber seals such as, for example, Viton7 seals developed by Dupont-Dow Elastomers, L.L.C., operable to withstand elevated temperatures while minimizing exposure to water and other elements.

In one embodiment, sensor or sensors 205 may include a thin film resistance temperature detector (RTD) operable to be positioned within an opening or cavity associated with sensor assembly 202. Such RTDs may be formed from platinum or other suitable materials. The RTD may include a front surface and a rear surface operable to be placed within an ambient environment. System 200 may include an Atmel AT90LS4434 processor with an integrated analog-to-digital function. The processor may be used to compare a precision reference resistor (not expressly shown) to one or more RTD sensors 205. The comparisons do not generally depend on battery supply voltage or temperature of the processor. Only relative resistance of sensors 205 and the reference resistor are compared. The sensitivity of a typical analog-to-digital conversion process may be approximately one count for each degree Fahrenheit change. The repeatability of measurements may be approximately +/−0.5 counts. Imbedded software in the processor's Flash ROM may compare A/D values to each temperature threshold or set point and appropriately control indicators 206 and 207. The reference resistor may be a precision metal-film resistor with a 0.1% accuracy, very low temperature coefficient and long-term stability. (For example, Panasonic: ERA-3YEBxxx, 1.5K Ohms)

For some applications, sensor 205 may include a thin-film ceramic device (Minco S247 PFY, 1.0K Ohms at 0 Centigrade). Typical specifications include:
  Material: Platinum film on a thin aluminum oxide substrate with a fused-glass cover.
  Tolerance: 0.12% at 0 degree Centigrade (C) (About +/−0.8 degrees Fahrenheit (F).
  Sensitivity: RTC=0.00385 Ohms/Ohm/degree C. (About 0.2% per degree F.).
  Repeatability: +/−0.1 degree C. or better.
  Stability: Drift less than 0.1 degree C. per year.
  Temperature range: −70 to +600 degrees C.
  Vibration: Withstand 20 Gs minimum at 10 to 2000 Hz.
  Shock: Withstand 100 Gs minimum sine wave shock for 8 milliseconds.
  The calculated accuracy of system 200 may be approximately four (4) degrees Fahrenheit, including reference resistor and sensor tolerances. The overall accuracy of system 200 may be rated at +/−10 degrees Fahrenheit.
  Sensor assembly 202 may include a cavity or opening at or near the tip or end of sensor assembly as illustrated in FIGS. 4 and 5 to accommodate one or more sensors 205. As such, sensor assembly 202 may provide an air flow path operable to allow ambient air to flow through the cavity to exposed sensor or sensors 205 and associated thin film elements. Sensors 205 may be positioned away from a facemask or face shield (not shown) and within an ambient environment such that system 200 may consistently and accurately sense ambient temperatures.

FIG. 5 shows a rear view of sensor assembly 202 illustrated in FIG. 4. Sensor assembly 202 includes a plurality of screws 209 to couple the front and rear surfaces of sensor assembly 202 with each other. Though not illustrated, the front and rear surfaces may be realized as a one-piece molded unit which may not require use of screws 209. Aperture 204 and mounting channel 210 may be operable to mount sensor assembly 202 to various types of safety equipment. Sensor assembly 202 also includes first indicator 206 and second indicator 207 operable to provide visible indications of various conditions such as temperature, hazardous materials, explosive mixtures, and/or radioactive nuclides detected by system 200.

In one embodiment, sensor assembly 202 may include rounded surfaces which may reduce snagging or jarring of sensor assembly 202 during use. Sensor assembly 202 may include a front surface made of a dark material and a rear surface made of an optically transmittable or substantially clear material which may include a micro-prism high-visibility surface finish to enhance visibility of indicators 206 and 207. Indicators 206 and 207 may also include optical transmission channels operable to transmit light to exterior surface of indicators 206 and 207. In this manner, a wearer may view indicators 206 and 207 when illuminated, while other personnel proximal to the wearer may also view illuminated indicators 206 and 207 via respective optical transmission channels. For example, indicators 206 and 207 may be visible to other firefighters from the front of sensor assembly 202 by illuminating indicators 206 and 207 which include optical transmission channels or light conducting paths to exterior portions of indicators 206 and 207 as illustrated in FIG. 4. As such, both the wearer and other personnel may view an indication representing a critical condition.

System 200 preferably includes a control unit disposed within housing 201 with electronics operable to communicate a signal associated with environmental and/or physiological conditions such as equipment temperature, ambient temperature or heart rate. Cable 203 may be communicatively coupled between sensor assembly 202 and housing 201. In one embodiment, sensor 205 may be operable as an "active" temperature sensor to provide continuous monitoring of ambient temperature by sampling on a periodic basis (e.g. every four seconds, eight seconds, etc.). In this manner, a detected ambient temperature condition may then be used to determine if an operating mode of system 200 should be altered. For example, system 200 may be operable to sample an ambient temperature condition every eight seconds. Upon detecting a selected ambient temperature condition the sample rate may be increased (e.g. increase sampling from once every eight seconds to four times per second). As such, system 200 may be operable to satisfactorily monitor ambient temperature conditions while conserving energy of a power source, such as a battery, associated with system 200.

System 200 may be operable to provide a wearer with an indication of selected environmental conditions. For example, first indicator 206, operable as a green indicator, may be continuously illuminated during a safe temperature condition. Upon system 200 determining an unsafe ambient air temperature condition or other critical condition, and associated control unit may provide a signal to second indicator 206, operable as a red indicator, in response to the hazardous or potentially hazardous condition. Some examples of control units satisfactory for use with system 200 are shown in FIGS. 1, 3, 12 and 14. Other examples are discussed throughout this application. A hazardous or potentially hazardous condition may include an ambient temperature of five hundred degrees Fahrenheit. As such, system 200 may continuously illuminate second indicator 206 operable as a red indicator when an ambient temperature reaches or exceeds this limit.

FIG. 6 is a side view showing system 200 coupled to a facemask according to one embodiment of the present disclosure. System 200 may be coupled to a facemask 221 of self contained breathing apparatus 230. Sensor assembly 202 may be coupled to front portion of facemask 221 such that a wearer may view indicators 206 and 207 of sensor assembly 202. Housing assembly 201 with a control unit disposed therein may also include on/off and test button 213 for checking operating status of system 200 and may be operable to perform a battery test, determine battery life, perform system diagnostics, etc. Housing assembly 201 may be coupled to a facemask webbing 220 using clip 208 such that housing assembly 201 may be covered by a helmet or other safety headgear (not expressly shown).

Housing assembly 201 may be coupled to sensor assembly 202 via cable 203 which may be positioned behind or along a portion of facemask 221 and facemask webbing 220. Cable 203, sensor assembly 202 and housing assembly 201 are preferably made of high quality materials capable of withstanding high temperature levels for extended periods of time (e.g. greater than five hundred degrees Fahrenheit for several minutes). System 200 advantageously allows a wearer to position system 200 such that, during use, system 200 may be comfortably worn in addition to being easy to attach or remove as required. System 200 provides one example of a personal situation awareness device which may be used with different types of safety equipment without having to be permanently mounted to such safety equipment.

FIGS. 8, 9, 10A and 10B show various alternative fastener systems which may be used to releasably attach all or portions of a personal situation awareness device and other safety systems with a facemask or other safety equipment in accordance with teachings of the present disclosure. For some applications facemask 221 may include frame 223 formed from metal alloys or other materials satisfactory for use in a high temperature, fire fighting environment. The dimensions associated with mounting channel 210 of sensor assembly 202 are preferably selected to be compatible with corresponding dimensions of frame 223. The dimensions and configuration of mounting channel 210 may be modified to accommodate various types of sensor assemblies, facemasks and other types of safety equipment.

Figure 8:
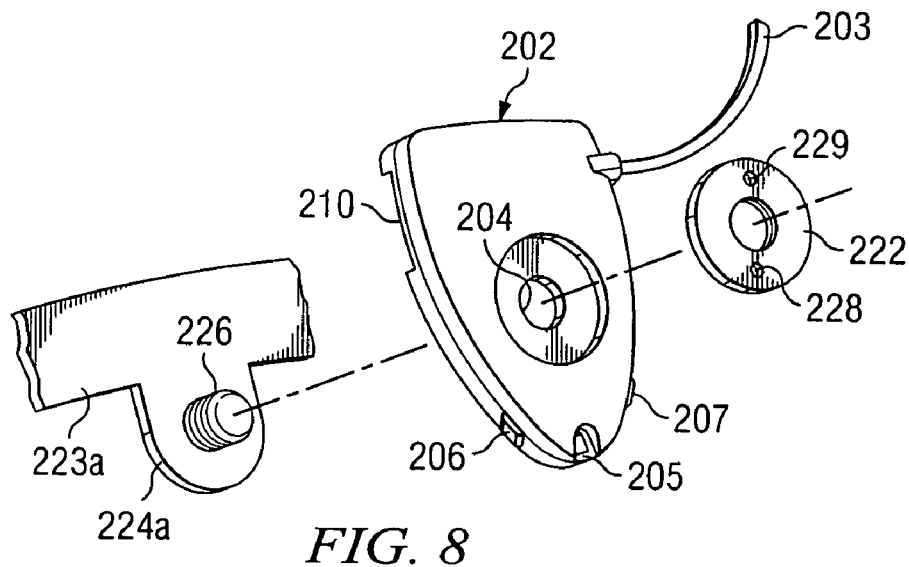
FIG. 8 is a schematic drawing showing an exploded, isometric view of a fastener system satisfactory for attaching a sensor unit incorporating teachings of the present disclosure with a facemask.

FIG. 8 is a schematic drawing showing an exploded, isometric view of a fastener system satisfactory for use in attaching sensor assembly or sensor unit 202 with facemask 221 in accordance with teachings of the present disclosure. For the embodiment shown in FIG. 8, frame 223a may include enlarged portion 224a which is formed as an integral component of frame 223a. For the embodiment shown in FIG. 8, threaded post or threaded stud 226 may be attached to enlarged portion 224 and project therefrom. Various types of mechanical fasteners other than threaded post 226 may be satisfactorily mounted on enlarged portion 224a.

The dimensions associated with aperture 204 of sensor assembly 202 and threaded post 226 are preferably selected to be compatible with each other to allow sensor assembly 202 to be releasably attached to or mounted on facemask 221. Threaded washer 222 may be used to releasably secure sensor assembly 202 with threaded post 226. For the embodiment shown in FIG. 8 threaded washer 222 preferably includes two small holes, 228 and 229, which may be engaged by an appropriately sized tool (not expressly shown) to secure threaded washer 222 with threaded post 226. Various types of nuts and other threaded fasteners may also be used.

Figure 9:
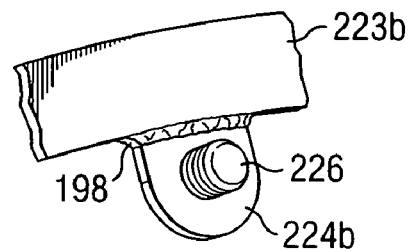
FIG. 9 is a schematic drawing showing an isometric view of another example of a fastener satisfactory for attaching a sensor assembly incorporating teachings of the present disclosure with a facemask.

FIG. 9 is a schematic drawing showing another example of a fastener assembly satisfactory for use in attaching a sensor unit or a sensor assembly with a facemask in accordance with teachings of the present disclosure. For the embodiment shown in FIG. 9, frame 223b may have approximately the same dimensions and configuration as frame 223a. Enlarged portion 224a and 224b may also have approximately the same dimensions and configuration. However, for the embodiment shown in FIG. 9 enlarged portion 224b may be attached with associated frame 223b using various types of bonding techniques. For example, frame 223b and enlarged portion 224b may be attached to each other by forming weld 198. For other applications a high temperature adhesive bond (not expressly shown) may be satisfactorily used to securely engage enlarged portion 224b with frame 223b. Threaded post or threaded stud 226 extends from enlarged portion 224b for use in releasably attaching a sensor assembly or sensor unit thereto in accordance with teachings of the present disclosure.

Figure 10A:
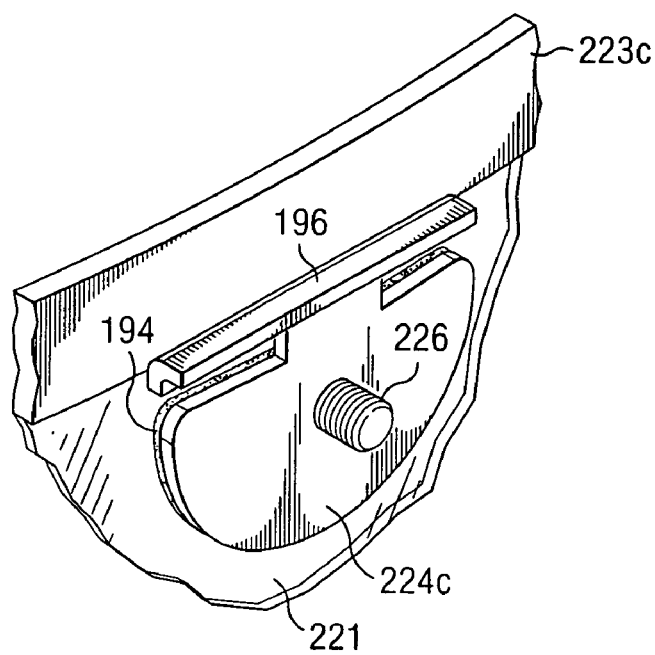
FIGS. 10A and 10B are schematic drawings showing an isometric view and a side view with portions broken away of an adapter which may be adhesively bonded with a facemask to releasably attach a sensor unit or sensor assembly with the facemask in accordance with teachings of the present disclosure.
Figure 10B:
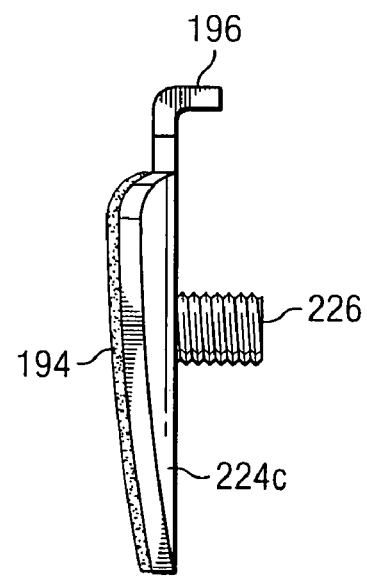

FIGS. 10A and 10B are schematic drawings which show still another fastener system satisfactory for use in attaching a sensor unit or sensor assembly with a facemask or other types of safety equipment in accordance with teachings of the present disclosure. For the embodiments shown in FIGS. 10A and 10B enlarged portion 224c may be securely mounted on facemask 221 using various types of high temperature adhesives. The embodiment shown in FIGS. 10A and 10B eliminates the requirement to form enlarged portion 224c as an integral component of frame 223c or to directly attach enlarged portion 224c with frame 223c.

Enlarged portion 224c may be formed from various types of metal alloys and/or high temperature polymeric materials satisfactory for use with a facemask associated with fire fighting equipment. Enlarged portion 224c preferably includes a generally curved or arcuate portion compatible with the exterior surface of facemask 221. See FIG. 10B. Threaded fastener or stud 226 may be formed on or attached to enlarged portion 224c using various techniques which are well known in the art. For the embodiment shown in FIGS. 10A and 10B, enlarged portion 224c preferably includes upper support 196 selected to be compatible with exterior dimensions of sensor assembly or sensor unit 202. High temperature adhesive bond 194 is preferably formed between the exterior of facemask 221 and an adjacent interior surface of enlarged portion 224c. Various types of adhesive materials such as 3M Corporation's Type 5952 adhesive foam sheets may be satisfactorily used to form adhesive bond 194. 3M Corporation's adhesives numbered 4611, 4646 and 4655 may also be used for form bond 194.

The dimensions of enlarged portions 224a, 224b and 224c may be substantially modified to accommodate various types of facemasks, face shields and other types of safety equipment. Also, the dimensions and configurations of enlarged portions 224a, 224b and 224c may be modified to accommodate various types of personal situation awareness devices. For some applications housing assembly 201 and sensor assembly 202 may be combined as a single unit (not expressly shown) and mounted on enlarged portion 224a, 224b or 224c.

Figure 11:
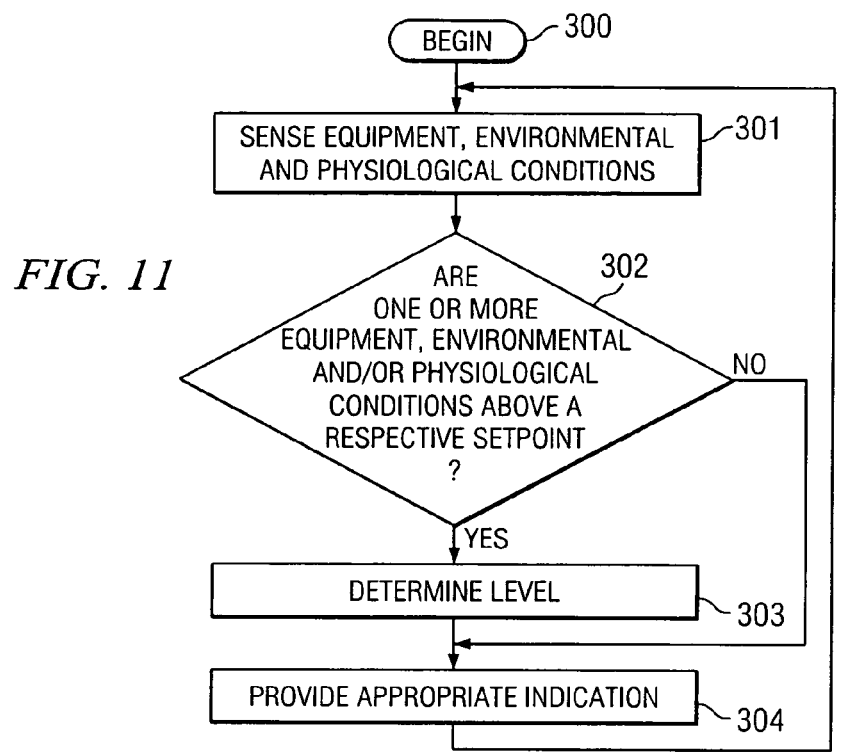
FIG. 11 is a flow chart showing a method to alert safety personnel of hazardous or potentially hazardous conditions according to another embodiment of the present disclosure.

FIG. 11 is a flow chart showing one method to alert personnel of hazardous or potentially hazardous conditions according to another embodiment of the present disclosure. The method may be used by systems 10, 80, 200, 500 and/or other safety system incorporating teachings of the present disclosure. The method begins generally at step 300. At step 301 equipment, environmental and physiological conditions may be sensed using various sensors such as a resistive temperature device (RTD), thermistor, infra-red (IR) sensor, air pressure, air flow rate monitor, heart rate detector, blood pressure sensor, or other sensors operable to sense selected equipment, environmental and physiological conditions. After sensing equipment, environmental and physiological conditions, the method determines at step 302 if the equipment, environmental and physiological conditions are greater than a respective set point.

After determining if equipment, environmental and physiological conditions are greater than one of the set points, the method proceeds to step 303 where the method determines the level of the measured equipment, environmental and/or physiological condition. The method, operable to determine equipment, environmental and physiological conditions, may provide several different types of indications depending on the determined conditions as they relate to, for example, safety procedures. The method may be operable to determine a plurality of equipment, environmental and physiological conditions or thresholds to provide various indications based upon the respective set points. For example, one group of set points may include an ambient air temperature between one hundred forty degrees Fahrenheit and two hundred degrees Fahrenheit; an ambient air temperature above two hundred degrees Fahrenheit for a period of eight seconds; an ambient air temperature between four hundred degrees Fahrenheit and five hundred degrees Fahrenheit; an ambient air temperature above five hundred degrees Fahrenheit for eight seconds; or a plurality of other air ambient temperature conditions as needed.

Upon determining a level at step 303, the method proceeds to step 304 where the method may provide an appropriate indication for the determined level. For example, the method may determine an ambient air temperature condition of two hundred degrees Fahrenheit for a period of eight or more seconds. As such, the method may continuously illuminate indicator 206 which may be operable as a green light emitting diode or a miniature incandescent light. In another embodiment, an ambient air temperature condition between four hundred degrees Fahrenheit and five hundred degrees Fahrenheit may be determined. As such, first indicator 206 operable as a green Indicator may be continuously illuminated and second indicator 207 operable as a red indicator may be periodically illuminated (e.g. blinking) thereby providing an overall indication reflective the associated determined level.

Upon providing an appropriate indication at step 304, the method proceeds to step 301 where the method senses additional equipment, environmental and physiological conditions. In this manner, the method provides for sensing equipment, environmental and physiological conditions determining a level and providing an appropriate indication based upon the sensed conditions to ensure that safety personnel have current indications of any hazardous or potential hazardous condition.

In one embodiment, a system deploying the method of FIG. 11 may be operable to sample selected equipment, environmental and physiological conditions. The system may be operable in a mode which senses temperature at a periodic rate based upon a determined temperature level. For example, the system may sense a selected temperature every eight seconds until a temperature level of one hundred degrees Fahrenheit is sensed. As such, the system may alter the operating mode to sense the same temperature four times per second. In this manner, effective life of an associated battery may be preserved during what may be "non-critical" temperature conditions to extend the amount of time the system may be used.

Figure 12:
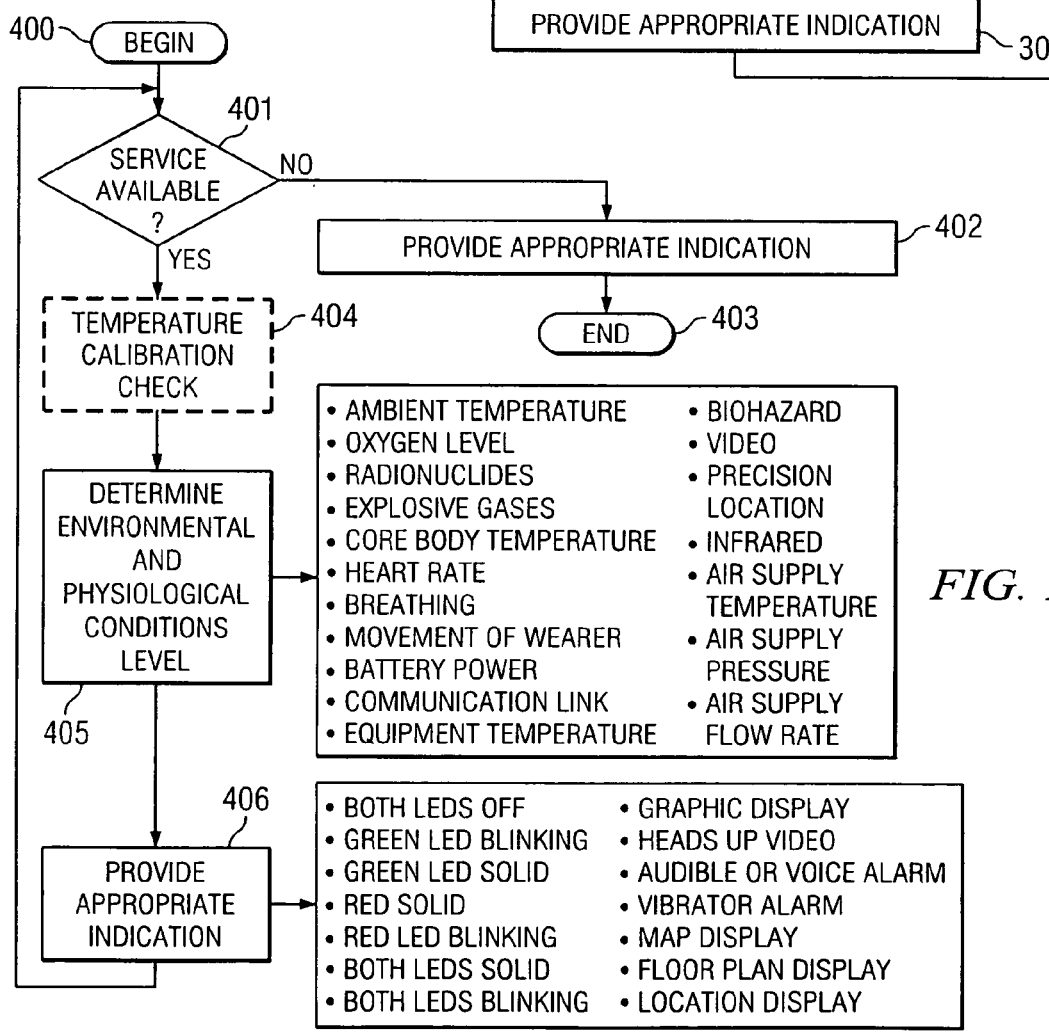
FIG. 12 is a flow chart showing a method to identify, monitor, evaluate and alert personnel of hazardous or potentially hazardous conditions according to teachings of the present disclosure.

FIG. 12 is a flow chart of a method for activating a system or device to alert a user of hazardous or potentially hazardous conditions according to one embodiment of the present disclosure. The method may be deployed by systems 10, 80, 200, 500 and/or any other system operable to deploy the method illustrated in FIG. 12. Reference numbers, components, and elements of system 200 of FIG. 4 are used in an exemplary form but are not intended to limit the applicability of the method of FIG. 12.

The method begins generally at step 400. At step 401, the method determines if service is available for measuring selected equipment, environmental and physiological conditions using a system or device such as system 200. For example, a voltage regulator (not expressly shown) associated with system 200 may determine the amount of power available for operating system 200. For example, a "power-consumption-to-operating-time" ratio may be provided for determining service availability. In one embodiment, fifteen minutes of service must be available prior to providing service for a system. If an appropriate amount of operating time or service is not available, the method may deny service and proceed to step 402 where an appropriate indication may be provided to a user. For example, both first indicator 206 and second indicator 207 may blink three times indicating that service is not available due to a weak battery or power source.

In one embodiment, the method at optional step 404 may perform a diagnostic check of an associated system prior to providing service. For example, the method may perform a diagnostic check of electronics and associated hardware prior to allowing service. One embodiment may also allow a wearer to initiate a system check or a battery test prior to using the system.

Figure 13:
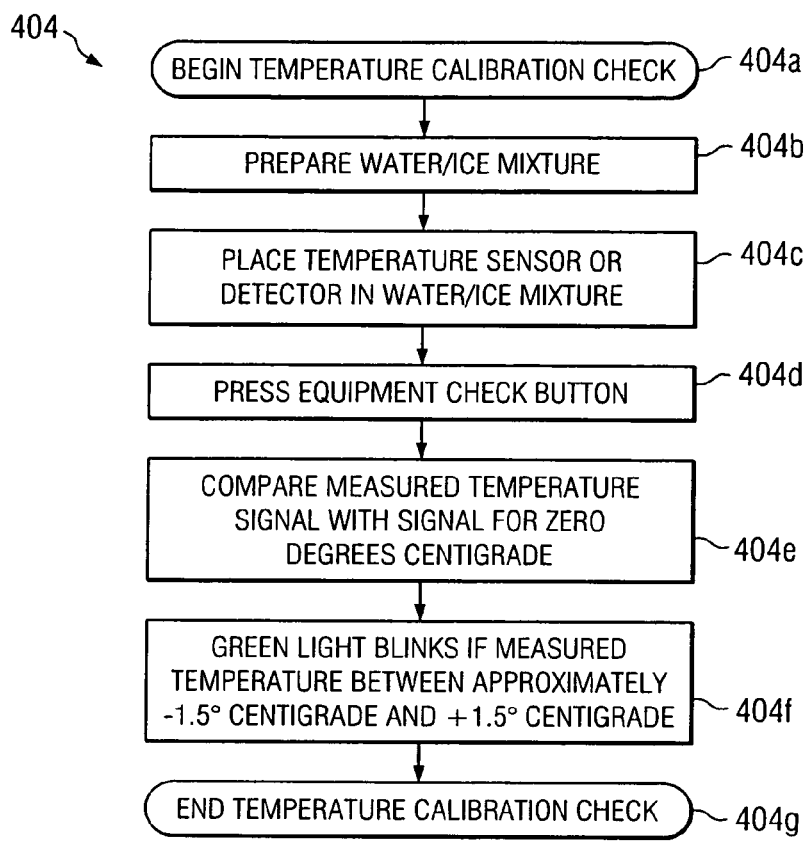
FIG. 13 is a block diagram showing one method to perform a calibration check in accordance with teachings of the present disclosure.

FIG. 13 shows one example of a method to perform a calibration check at step 404. Other types of diagnostic checks may be performed in accordance with teachings of the present disclosure. An associated control unit may detect when an associated "equipment check" or "test" button is held down. When the button is held, the control unit and associated software measure the temperature of an ice and water mixture and compare the measurement to a reference value for zero degrees Centigrade. If the measurement is close to zero, the unit is calibrated and the control unit may blink one or more green lights.

To perform a calibration check in the field, the method shown in FIG. 13 may start with step 404a. At step 404b, a mixture of finely crushed ice and water may be prepared in an insulated container, such as a plastic foam cup. Sensors 205 may be immersed in the ice/water mixture at step 404c with the tip of sensor 205 near the center of the ice. After 5 minutes the temperature will stabilize. The test button or check button is pressed and held at step 404d. The associated system at step 404e may then compare measured temperature signals from sensor 205 with a reference signal corresponding with zero degrees Centigrade or thirty-two degrees Fahrenheit. At step 404f, both indicator lights 206 and 207 will blink three times and then the green light will blink if the system is satisfactorily calibrated. The green light will continue to blink at step 404f as long as the test button is held and the temperature of sensor 205 remains between thirty and thirty-four degrees Fahrenheit. At step 404g, the test button may be released and the calibration check will end.

After determining that service is available at step 401 and performing an optional diagnostic check at step 404, the method may then proceed to step 405 where the method determines the value of selected environmental and physiological conditions. For example, system 200 having sensor assembly 202 may sense a temperature using sensors 205. Upon sensing the temperature, a temperature level may then be determined based upon the sensed temperature. For example, a comparator may be used in association with sensor assembly 202. A converted signal representing the sensed temperature may then be used to determine the temperature level.

In one embodiment, several temperature levels or thresholds may be used to determine a temperature level. For example, one embodiment may include determining an ambient air temperature of one hundred forty degrees Fahrenheit; between one hundred forty degrees Fahrenheit and two hundred degrees Fahrenheit; greater than two hundred degrees Fahrenheit for eight seconds; between four hundred degrees Fahrenheit and five hundred degrees Fahrenheit; and greater than five hundred degrees Fahrenheit for eight seconds. Other temperature levels or thresholds may be used in association with the method of FIG. 12 as desired.

Upon determining a temperature level, the method may proceed to step 406 where the method provides an appropriate indication for the determined level. For example, system 200 having first indicator 206 operable as a green indicator and second indicator 207 operable as a red indicator may be used to provide an appropriate indication of the determined temperature level or temperature condition at step 405. As such, the method may use several combinations for illuminating first indicator 206 and second indicator 207. For example, the method may not illuminate either indicator for a temperature of less than one hundred and forty degrees Fahrenheit; periodically illuminate (e.g. blinking) first indicator 206 for a temperature level between one hundred forty degrees Fahrenheit and two hundred degrees Fahrenheit; continuously illuminate first indicator 206 for a temperature level of greater than two hundred degrees Fahrenheit for eight seconds; continuously illuminate first indicator 206 and periodically illuminate (e.g. blinking) second indicator 207 for a temperature level between four hundred degrees Fahrenheit and five hundred degrees Fahrenheit; or continuously illuminate first indicator 206 and second indicator 207 for a temperature of greater than five hundred degrees Fahrenheit for eight seconds.

Upon providing an appropriate indication, the method proceeds to step 401 where the method determines another temperature level. In this manner, several different temperature levels and associated indications may be determined and provided by the method of FIG. 12 as needed or required while providing indications of ambient air current temperature conditions to safety personnel.

Figure 14:
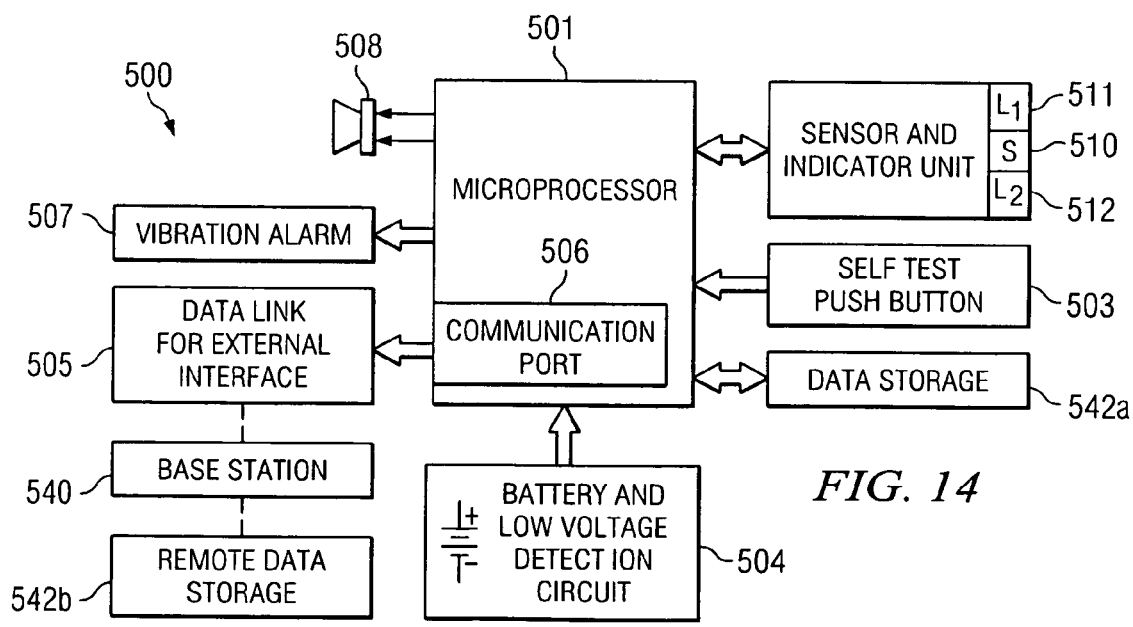
FIG. 14 is a block diagram of a system operable to identify, evaluate, monitor and alert personnel of hazardous or potentially hazardous conditions according to another embodiment of the present disclosure.

FIG. 14 is a block diagram of a system for alerting safety personnel of hazardous or potentially hazardous conditions according to another embodiment of the present disclosure. In the embodiment of FIG. 14, system 500 may include microprocessor 501 operable to receive power from battery and low voltage detection circuit 504.

One alternate and acceptable implementation for microprocessor 501 would be to use multiple digital signal processors, microprocessors and/or microcontrollers as the control unit for system 500. For example, one microprocessor might be a digital signal processor (DSP) for use in conditioning certain sensor signals, while a second general-purpose microprocessor or microcontroller might control the overall sequencing and display of events for the system.

In one embodiment, system 500 may provide a battery life of greater than four months at room temperature thereby reducing the need for replacing a battery on a frequent basis. Microprocessor 501 may serve as a control unit for system 500, which may include alternate types of control devices as mentioned above. Service of system 500 may be automatically determined by processor 501 or may also be determined by operating self test push-button 503. Sensor unit 502 may include first indicator 511, second indicator 512 and temperature sensor 510. Sensor unit 502 may be operable to measure temperature or any other desired environmental condition or physiological condition and may provide an output to a comparator circuit or A/D converter operably associated with microprocessor 501. Microprocessor 501 may also be operable to provide signals to first indicator 511 and second indicator 512.

System 500 may further include vibration alarm 507 (e.g., mechanical motor, solenoid) and audible alarm 508 operable to provide an indication based upon a critical condition. Further, microprocessor 501 may include communication port 506 which is operable to output data to data link 505 to connect or communicate between system 500 and other external systems such as command center or base station 540. Data link 505 may use various communication technologies such as wireless, infrared, laser, fiberoptic, acoustic or cable. Data link 505 may also be used to communicate with another person wearing a second system 500. As such, a recorded temperature history or other pertinent information may be obtained by an external device operable to communicate with system 500 via data link 505.

During use, service or availability of system 500 may be determined by microprocessor 501 through accessing battery and low voltage detection circuit 504. Upon determining if sufficient voltage or battery life is available, system 500 may determine the value of selected environmental and physiological conditions using sensor unit 502 and multiple sensors 510. Microprocessor 501 may determine an operating mode for system 500 by sampling environmental and physiological conditions using sensor unit 502 and providing an operating mode based upon one or more selected conditions. For example, system 500 may sample or sense ambient temperature every eight seconds for temperatures less than one hundred forty degrees Fahrenheit, and four times per second for temperatures greater than one hundred forty degrees. As such, energy may be conserved at lower temperatures thereby extending the usable life of system 500's battery.

System 501, upon sensing a temperature with sensor unit 502, may then determine an ambient air temperature condition and provide an appropriate output. For example, if a temperature between one hundred forty degrees Fahrenheit and two hundred degrees Fahrenheit is determined, system 500 may provide one of a plurality of outputs available to system 500 such as using vibration alarm 507, audible alarm 508, indicators 511, 512. As such, system 500 provides an efficient system for providing personnel an indication of current ambient air temperature conditions. Indicators 511 and 512 may be light emitting diodes, liquid crystal displays, portions of a head up display or any other appropriate visual display for communicating information from system 500 to a wearer or user.

For some environments, such as a fire in a large building or other type of structure, ambient air temperature conditions may vary significantly from one location to the next. Ambient air temperature may also vary significantly, when a firefighter moves between a standing position and a crouched position. Also, a relatively quick response from indicators 511 and 512 may be desirable when a firefighter moves between safe ambient air temperature conditions and dangerous ambient air temperature conditions. For such applications, indicators 511 and 512 of system 500 may be operated as follows.

For safe ambient air conditions or other safe operating conditions, indicators 511 and 512 would both be green. When ambient air conditions or other environmental and/or physiological conditions are dangerous, both indicators 511 and 512 will preferably be red. When ambient air temperatures or other environmental and/or physiological conditions are rising, indicators 511 and 512 will preferably remain solid. When ambient air temperatures or other environmental and/or physiological conditions are decreasing, indicators 511 and 512 will preferably be blinking. For example, as a firefighter moves through a building with safe, but increasing ambient air conditions, both indicators may be solid green. If safe ambient air temperatures are decreasing, indicators 511 and 512 may both be green and blinking. In a similar manner, if the firefighter is in an ambient temperature condition above established limits and the temperature is continuing to increase, indicators 511 and 512 may be red and solid. If ambient air temperature conditions are above an established safety limit, but decreasing or cooling, both indicator 511 and 512 may be red and blinking. The response time to increasing or decreasing temperature would be relatively quick, often less than one (1) second. Therefore, when the change in indicator 511 and 512 from solid to blinking or blinking to solid would quickly advise a firefighter that the ambient temperature conditions are changing.

Figure 15A:
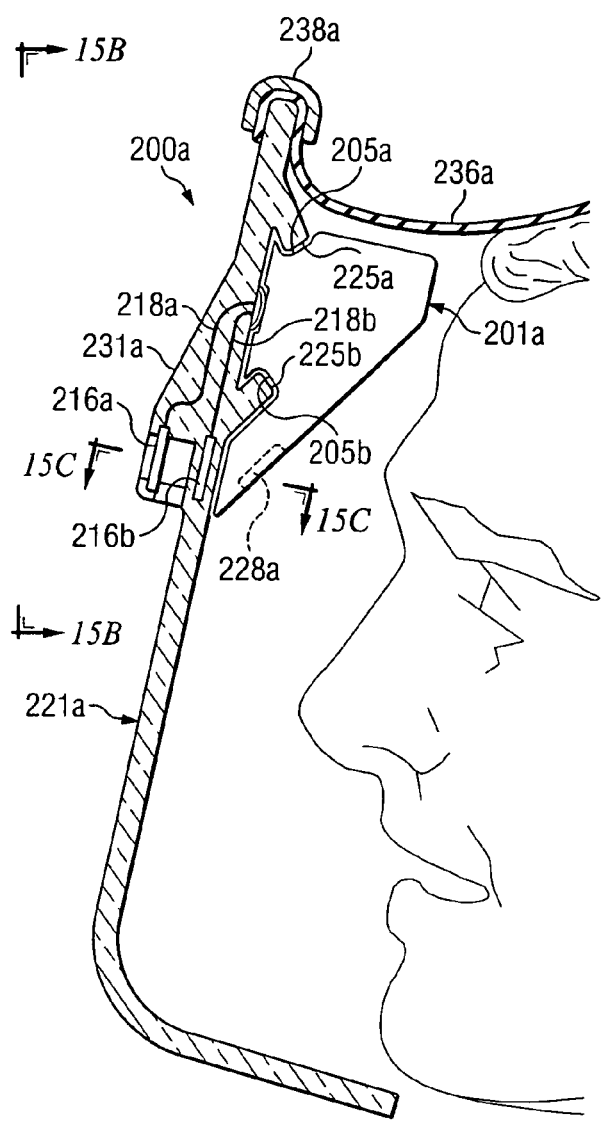
FIG. 15A is a schematic drawing in section with portions broken away showing one example of a facemask or lens having an integrated system satisfactory for identifying, monitoring and evaluating environmental, physiological and/or associated equipment conditions in accordance with teachings of the present disclosure.
Figure 15B:
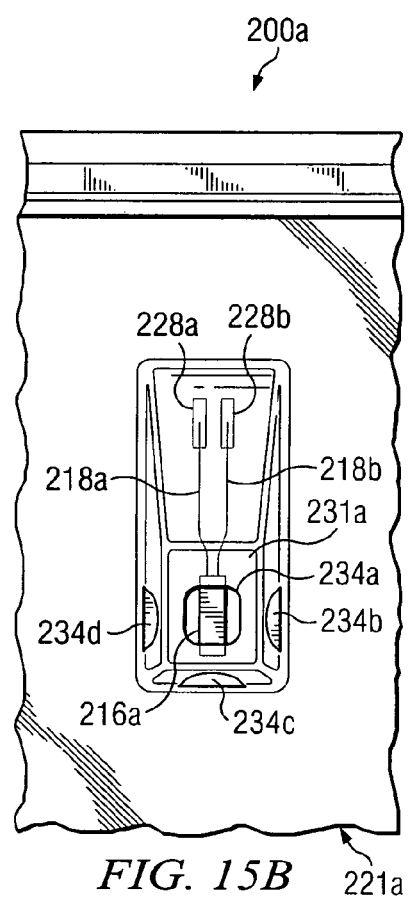
FIG. 15B is a schematic drawing showing an isometric view with portions broken away taken along lines 15B-15B of FIG. 15A.
Figure 15C:
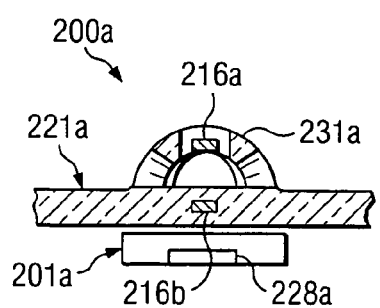
FIG. 15C is a schematic drawing in section with portions broken away taken along lines 15C-15C of FIG. 15A.

FIGS. 15A, 15B and 15C are schematic drawings showing one example of a face mask having a control unit, multiple sensors and a visual display incorporating various features of the present disclosure. The facemask may be used with new equipment or may be used to replace a face piece, facemask or lens in existing equipment. For embodiments such as shown in FIGS. 15A, 15B and 15C face mask 221a may include a pair of sensors 216a and 216b. However, more than two sensors may be used as appropriate for each hazardous or potentially hazardous condition. As discussed later in more detail, first sensor 216a may be exposed to ambient conditions exterior to face mask 221a. Second sensor 216b may be disposed within portions of face mask 221a to monitor the status of face mask 221a. For other applications second sensor 2116b may be disposed on interior portions of face mask 221a to monitor the environment adjacent to a wearer's face (not expressly shown). Alternatively, second sensor 216b may be disposed in other portions of protective equipment associated with face mask 221a (not expressly shown).

System 200a such as shown in FIGS. 15A, 15B and 15C may include various features and characteristics as previously described with respect to system 200. System 200a may be operable to provide a wearer with an indication of selected environmental conditions and/or equipment conditions. For example, first sensor 216a may be operable to detect temperatures exterior to face mask 221a and second sensor 216b may be operable to detect the temperature of face mask 221a or other protective equipment. For other applications first sensor 216a may be used to monitor for various types of gas mixtures, potentially hazardous biological materials and/or the presence of nuclear radiation. Second sensor 216b may be disposed within interior portions of face mask 221a to determine if the environment immediately adjacent to a wearer contains such gas mixtures, potentially hazardous biological materials and/or nuclear radiation. Face mask 221a may be used with various types of equipment, including, but not limited to, self contained breathing apparatus.

Various types of control units as previously discussed in this application may be satisfactorily used with system 200a. One or more control units may be disposed within housing 201a and connected with sensors 216a and 216b by respective wires 218a and 218b. For some applications the size of sensors 216a and 216b may be approximately 0.1×0.3×0.2 inches. Wires 218a and 218b may sometimes be 30-gauge copper wire.

For some applications housing 201a may be releasably engaged with interior portions of face mask 221a. Housing 201a may sometimes be described as a "snap in" control unit.

Various techniques, including, but not limited to grooves 205a and 205b formed on the exterior of housing 201a and corresponding projections 225b and 225c extending from interior portions of face mask 221a may be used. For other applications (not expressly shown) the control unit and associated display 228a may be molded into a portion of facemask 221a.

A pair of contacts 228a and 228b may be formed on the interior surface of face mask 221a for engagement with corresponding contacts (not expressly shown) on the exterior of housing 201a. Signals may be communicated from sensors 216a and 216b via respective wires 218a and 218b to associated contacts 228a and 228b. The control unit disposed within housing 201a may analyze such signals and provide appropriate information for a wearer on display 228a. Some applications display 228a may include indicators 51 and 52 as previously described with respect to system 200. For other applications display 228a may provide information such as previously described with respect to systems 10, 80, and 500.

Display 228a may be integrated into housing 201a as part of the control unit. For other applications display 228a may be molded into a different part of facemask 221a (not expressly shown). Housing or control unit 201a may have a curved shape to fit inside of facemask 221a and to be compatible with the forehead of a wearer. Except for protrusion 231a, sensors 216a and 216b and projections 225a and 225b, facemask 221a may have the same characteristics and features of commercially available facemasks.

For some applications the exterior portion of face mask 221a may include protruding portion 231a. Wires 218a, 218b and/or first sensor 216b may be disposed within protruding portion 231a. Also, multiple openings 234a, 234b, 234c and 234d along with associated passageways may be formed in protruding portion 231a. Openings 234a-234d and associated passageways cooperate with each other to allow exposing first sensor 216a to the ambient environment adjacent to the exterior of face mask 221a and to allow movement of surrounding air therethrough.

Various types of material 236a may be attached with face mask 221a by an appropriate clamp or other type of seal 238a. The type of material selected and the type of clamp selected will often depend upon the environment in which face mask 221a is used. For some applications clamp 238a and material 236a may be selected to be compatible with self contained breathing apparatus, helmets and other protective equipment worn by firefighting personnel.

Personal situation awareness devices and other systems incorporating teachings of the present disclosure may have the following components, features and characteristics.

Temperature Encoders

An electronic thermometer that tells firefighters about the temperature of the environment. Critical temperature thresholds may be indicated with a system of green and red lights in the periphery of their vision.

Measures a combination of the air temperature and radiant heat flux to predict the surface temperature trend at the mask faceplate.

Thermal sensor element is a thin-film platinum RTD on a thin ceramic chip. It can predict, by up to 30 seconds, the temperature the firefighter's gear will soon experience.

Measures air supply temperature to a facemask.

Provide firefighters information about critical conditions inside a structure fire.

Provide a training tool to allow certain basic training exercises to be easily repeated without having to travel to and go into a burn-box trainer, saving cost, time, and potential equipment damage and personnel injury.

EXAMPLE 1 OF INDICATED CONDITIONS

| Light Status | Department Determined Policy/Procedures |
| --- | --- |
| No Lights | Less than 125 Fahrenheit. Victims can survive. Proceed normally. |
| Blinking Green | You are in a warm environment and your fire protective gear should be safe. Unprotected victims can survive only a few minutes. Cool the area. Proceed normally. |
| Solid Green | You are depending on the thermal barrier of your protective clothing but it is safe to continue. Most turnouts are rated for 10 or 12 minutes of protection at 212 F.. Steam burns can occur. Victims cannot survive without protection. Cool the environment. Get lower. |
| Solid Green, Blinking Red | Your gear is near its protection limit. Get lower. Cool the area immediately or move. Flashover is possible. |
| Solid Green, Solid Red | The Integrity of your protective gear is at risk. You are in serious jeopardy. Flashover is likely. Evacuate Immediately. |

EXAMPLE 2

| Light Status | Department Determined Policy/Procedures |
| --- | --- |
| Two Lights Both Green | You are in a safe environment and equipment conditions are below preselected safe limits. Proceed normally. |
| Two Lights Both Red | Ambient conditions or equipment conditions are above preselected safe limits. Victims may not survive without protection. Cool the environment. Get lower. |
| Both Lights Blinking (Green or Red) | Air temperature or other hazardous condition decreasing. |
| Both Lights Solid (Red or Green) | Air temperature or other hazardous condition increasing. |

Construction

Molded high-temperature plastics, involving the same materials used to make firefighter's masks and helmets.

Functional Characteristics

Calculates lag time between temperature of environment and temperature of safety equipment.

Calculates heat sink characteristics of safety equipment.

Calculates temperature grade gradient between external environment and safety equipment.

Calculates temperature limits based on lag time between external environment temperature and temperature of equipment.

Monitors and evaluates physiological characteristics (temperature, heart rate, breathing) of the user.

Adapter clip for attachment with facemask or with other types of safety equipment.

Multiple sensors such as temperature, infrared, acoustic, pressure, oxygen or other gases.

Embedded in molded plastic to conform with various types of safety equipment.

Thermal Encoder with Data Recording and Retrieval Capability

Analysis software receives, displays, coordinates, compares and analyzes.

A maintenance tool for product life cycle.

Number of exposures to critical environment

Monitor limit on number of equipment cycles

Time tracks for download allows for simultaneous comparison of multiple units exposed to a situation.

Records time above selected thresholds.

Real Time Telemetry.

Two-way data transmission and reception

Heads Up displays of information

Motion stop sensor

Time stamp

Analysis software and analysis tools for command station.

Real time telemetry with personnel tracking and hazard plotting.

Sensors, transmitters, a receiver that tracks environmental conditions, physiological conditions, locations and movements.

Forward looking infrared Heads up display, etc.

Software and hardware that collects, organizes, interprets, analyses, compares, alerts, records and communicates (send/receive) with remote locations and adjacent personnel.

Further examples of practical embodiments of this disclosure are listed and described below. These examples are representative of a family of devices with sensor and display functions and other capabilities that provide optimal situational awareness for personnel in different targeted environments.

FE2000—Basic Unit
FE2001—adds recording and playback of history
FE2002—integrated into facemask lens
FE2003—adds physiological sensors
FE2004—adds communication via firefighter's walkie-talkie
FE2005—adds ability to receive commands from walkie-talkie and accept user's personal limits
FE2006—adds explosive-gas mixture sensor
FE2007—adds infrared video FE2000 Basic Unit Overview . . .

The FE2000 is a light-indicating thermometer that attaches to the top-center of a firefighter's face piece to sense and indicate temperature when fighting a structure fire.

Specifications . . .

General Product Description: Light Indicating Thermometer. Fire-Eye consists of a Sensor/Display piece fitted at the top of the mask faceplate and an electronic Clip-Box worn clipped at the back of the mask webbing, under the Nomex™ hood.

Design Application: For use with standard SCBA facemasks when fighting structure fires.

Temperature Sense Point: Near the center of the mask faceplate.

Temperature Sensing Element: Thin-film Platinum RTD on thin ceramic chip.

Temperature Sensing Rate: The sensor element is read four times per second when temperature conditions are being displayed.

Indicator Visibility: Green and Red indicator lights are visible through the facemask, centered just above the line of sight.

Indicated Temperature Conditions: The temperature conditions indicated depend on the environmental temperature, on the temperature of the surface of your protective gear and on the time spent at a particular temperature.

No Lights (below 125 F):
Proceed normally. Victims can survive. Act according to your Department's training and policies.

Green is Blinking slowly and is mostly off:
You are in a warm environment and your fire protective gear should be safe. Unprotected victims can survive only a few minutes. Act according to your Department's training and policies.

Green is Blinking faster and is 50% on:
The temperature is warmer and your fire protective gear should be safe. It is less likely that an unprotected victims could survive. Act according to your Department's training and policies.

Green is Blinking slowly and is mostly on:
The temperature is very warm. You are depending on the thermal barrier of your fire protective clothing. Cool the environment and act according to your Department's training and policies.

Solid Green:
The temperature is hot but your protective gear is safe for a few more minutes. Steam injury can occur. Unprotected victims cannot survive. Cool the area and act according to your Department's training and policies.

Red (in general):
Your gear is near its protection limit. Get lower. Cool the area immediately or move. Flashover is possible. Act according to your Department's training and policies.

Red is blinking:
The environment is hot but is cooling. Your gear is near its protective limit. Cool the area immediately or seek a cooler location. Act according to your Department's training and policies.

Red is solid:
The environment is hot and is still heating. The integrity of your protective gear is at risk. You are in serious jeopardy. Evacuate immediately to a cooler location. Flashover is likely. Act according to your Department's training and policies.

Early Red:
If the temperature increases very rapidly, Fire-Eye will display RED immediately without displaying all stages of GREEN. This warns quickly of extreme conditions. RED will be displayed until the rate of temperature increase slows.

Heat-soak Red:
If the temperature at the surface of your protective gear has been above 148 F for more than 15 minutes, Fire-Eye will display RED. This condition indicates that the protective capacity of your gear is likely nearing exhaustion. RED will blink if the temperature is decreasing and will be solid if the temperature is increasing. RED will continue to be displayed until the temperature cools below 125 F.

Temperature Accuracy: +/−5 Fahrenheit.

Temperature Response Rate: 2 degrees Fahrenheit per second when the temperature difference between the Fire-Eye Sensor and the environment is 20 degrees Fahrenheit. The higher the differential, the faster the response.

Battery Required: Two size AAA Alkaline cells.

Efficient Idle Mode: When the temperature is below 125 F, Fire-Eye reads the thermal sensor once every eight seconds to prolong battery life.

Expected Battery Life: 4 Months
Recommended Battery Replacement Interval: 2 Months
Equipment Check Features:
  Test Button for Electronics, Battery, and Lights
  Continuously monitors battery voltage
  Continuously monitors the connections to the temperature sensing element for open-circuit and short-circuit failures
  Battery-low or sensor failure is indicated by blinking both lights continually or by both lights off
  Built-in absolute calibration test for zero degree Centigrade standard
Absolute Calibration Check: Prepare a mixture of finely-crushed ice and water in an insulated container such as an 12-ounce foam cup. Immerse the Sensor/Display part of the Fire-Eye Temperature encoder in the ice/water mixture with the tip of the sensor near the center of the ice. Wait 5 minutes for the temperature to stabilize. Press and hold the test button. Both lights will blink 3 times and then the green light will blink if the Fire-Eye unit is accurately calibrated. The green light will continue to blink as long as the button is held and the temperature of the sensor remains between 30 and 34 degrees Fahrenheit.
Sensor/Display Operating Environment: Temperature 0 to 400 Fahrenheit. Waterproof.
Clip-Box Operating Environment: Temperature 0 to 185 Fahrenheit. Waterproof.
Temperature Endurance:
  Black Plastic Parts: Reduced Strength at 450, Melts at 650 Fahrenheit.
  Clear Plastic Parts: Reduced Strength at 350, Melts at 680 Fahrenheit.
  Teflon™ Cable: 20,000 Hour Service Life at 400 Fahrenheit.
Plastic Components:
  Black Plastic Parts: GE ULTEM 1000, UL File Number E121562; UL-94 rated V-O for 0.016 inch thickness; UL-94 rated V-5A for 0.075 inch thickness; CSA File Number LS88480.
  Clear Plastic Parts: GE LEXAN 4701R, UL File Number E121562; UL-94 rating HB for 0.058 inch thickness.

FE2001

Overview . . .
The FE2001 has all the features of the FE2000 plus the ability to record and report the temperature history of each firefighting event.
Specifications . . .
  Record Keeping: The FE2001 records temperature history during each firefighting event. Its internal memory has the capacity to store at least one hour's history. Recording begins automatically when the temperature exceeds 125 F. When the temperature decreases below 125 F, the recording is saved internally until the next firefighting event.
  Downloading Recorded Data: The FE2001 clip-box has an infrared serial port and can transfer recorded temperature history data to a suitably-configured personal computer for analysis. The clip-box port must be placed near the infrared port of the computer. The downloading process involves starting a receiver application on the personal computer and then double-clicking the FE2001 Equipment-Check button.
  Data Format: The temperature history data becomes a file on the hard disk of the personal computer. Each recorded temperature value is associated with a relative time value. The first temperature value recorded during a firefighting event will have a relative time of zero. Subsequent temperature values will have a relative time value indicating the number of seconds that have passed since the previous temperature value was recorded. The format of the temperature history will be such that it can be imported into a Microsoft Excel (or other) spreadsheet for analysis.
The FE2001 will transmit the following data to a personal computer via infrared beam when the Equipment-Check button is double-clicked:
  A unique serial number identifying the Fire-Eye unit.
  History of environmental temperature

FE2002

Overview . . .
The FE2002 has all the features of the FE2001 but, rather than being an add-on accessory, it is integrated into a firefighter's facemask.
Specifications . . .
  The FE2002 replaces the facemask lens in existing SCBA facemasks. All materials and dimensions are strictly compatible with the lens of each equivalent existing facemask.
  The FE2002 temperature sensor is molded into the upper surface of the face piece lens, just above the firefighter's line of sight.
  The electrical connections to the temperature sensor are molded into the face piece lens and terminate on the inner surface of the face piece lens near the firefighter's forehead.
  The FE2002 equivalent of the FE2001's clip-box, battery, display and electronics, here called the "controller", conforms to the shape of the inner surface of the face piece lens and snaps into flanges molded onto the inner surface of the face piece lens. The controller body is sized to fit in the space between the face piece lens and the firefighter's forehead. The controller has electrical contacts that align with the sensor contacts and has display lights positioned to be visible in the firefighter's peripheral vision. The Equipment-Check button and the infrared serial port are accessible on the inner side of the controller body when the facemask is not being worn.
  The FE2002 will transmit the following data to a personal computer via infrared beam when the Equipment-Check button is double-clicked:
    A unique serial number identifying the Fire-Eye unit.
    History of environmental temperature

FE2003

Overview . . .
The FE2003 is integrated into a firefighter's facemask in the same way as the FE2002. The FE2003 adds physiological monitoring to the FE2002's environmental temperature capabilities.
Specifications . . .
  The FE2003 replaces the facemask lens in existing SCBA facemasks. All materials and dimensions are strictly compatible with the lens of each equivalent existing facemask.
  The FE2003 is enhanced to measure heart-rate, body temperature and breathing rate and to display a visible alarm when dangerous physiological conditions occur due to personal overexertion or overheating.

Breathing rate is measured by a low-frequency microphone that senses the cyclic change in facemask air pressure as a firefighter breathes through his SCBA. The microphone is internal to the controller and makes it's measurements through a small hole in the controller body that is protected by a thin silicone rubber moisture barrier diaphragm.

To sense heart-rate and body temperature, a thin silicone rubber flap extends from the controller body and is worn against the firefighter's temple and under the facemask perimeter gasket. Molded into the flap is an RTD temperature sensor and a flexible piezoelectric pressure sensor. The temperature sensor measures the skin temperature of the firefighter in the area of his temple. The pressure sensor responds to the pulse of the temporal artery to measure heart-rate.

As with the FE2002, measurements are recorded internal to the controller and may be downloaded after a firefighting event into a personal computer through the use of an infrared serial port built into the controller body.

The FE2003 will transmit the following data to a personal computer via infrared beam when the Equipment-Check button is double-clicked:
A unique serial number identifying the Fire-Eye unit.
History of environmental temperature
History of body temperature
History of heart-rate
History of breathing rate

FE2004

Overview . . .

The FE2004 is integrated into the firefighter's facemask in the same way as the FE2003. The FE2004 adds a motion sensor and a connection to the firefighter's walkie-talkie to the FE2003's environmental temperature and physiological measurement features.

Specifications . . .

The FE2004 replaces the facemask lens in existing SCBA facemasks. All materials and dimensions are strictly compatible with the lens of each equivalent existing facemask.

The motion sensor is an integrated circuit accelerometer internal to the FE2004 controller body. The sensor will determine if a firefighter has become immobilized.

The FE2004 controller body provides a connector which provides a signal to a compatible walkie-talkie. Whenever the firefighter presses the "talk" button of the walkie-talkie, a burst of FE2004 data may be transferred during the first few milliseconds of the transmission. The data transferred consists of:
A unique serial number identifying the firefighter.
Current environmental temperature
Current body temperature
Current heart-rate
Current breathing rate
Current activity status (mobile or immobile)

If the firefighter is sensed to be immobile or does not press the "talk" button of his walkie-talkie for some time, the FE2004 will automatically initiate transmission of bursts of data. In the absence of firefighter action, periodic transmissions will occur at a preset time interval.

A suitable base station, in conjunction with a personal computer, can receive and log the FE2004 data for each firefighter and can display any alarm conditions to the base station operator.

The FE2004 will transmit the following data to a personal computer via infrared beam when the Equipment-Check button is double-clicked:
A unique serial number identifying the Fire-Eye unit.
History of environmental temperature
History of body temperature
History of heart-rate
History of breathing rate
History of activity status

FE2005

Overview . . .

The FE2005 is integrated into the firefighter's facemask in the same way as the FE2004. In addition to the data transmission features of the FE2004, the FE2005 has the ability to accept burst digital data from the firefighter's walkie-talkie. The FE2005 also adds the capability to be preset with the firefighter's personal physiological "redline", so that an appropriate alarm may be displayed for each individual firefighter if he becomes overexerted.

Specifications . . .

The FE2005 replaces the facemask lens in existing SCBA facemasks. All materials and dimensions are strictly compatible with the lens of each equivalent existing facemask.

Like the FE2004, the FE2005 will transfer a burst of data to the walkie-talkie when the firefighter presses the "talk" button. The FE2005 will also transfer data to the walkie-talkie if the FE2005 receives a "query" command from the walkie-talkie. The data transferred consists of:
A unique serial number identifying the firefighter.
Current environmental temperature
Current body temperature
Current heart-rate
Current breathing rate
Current activity status (mobile or immobile)

Alarm messages received from the walkie-talkie by the FE2005 will be seen by the firefighter via the FE2005 alarm display. The following are typical alarm messages that may be sent to the FE2005 by the walkie-talkie base station operator.
General Mayday "everyone leave the structure" message
Personal Mayday "you leave the structure" message
Personal "you check your buddy" message The nature of the message may be discerned in the blinking pattern of the FE2005 alarm lights or, optionally, in a more sophisticated character-oriented or graphical heads-up display.

The FE2005 will transmit the following data to a personal computer via infrared beam when the Equipment-Check button is double-clicked:
A unique serial number identifying the Fire-Eye unit.
History of environmental temperature
History of body temperature
History of heart-rate
History of breathing rate
History of activity status

FE2006

Overview . . .

The FE2006 is integrated into the firefighter's facemask in the same way as the FE2005. The FE2006 adds an explosive-gas mixture sensor and the ability to display an additional alarm pattern to the capabilities of the FE2005.

Specifications . . .

The FE2006 replaces the facemask lens in existing SCBA facemasks. All materials and dimensions are strictly compatible with the lens of each equivalent existing facemask.

A gas-mixture sensor is molded into the outside surface of the facemask lens above the firefighter's line of sight near the position of the FE2005's environmental temperature sensor.

When the sensor determines that a potentially-combustible gas mixture is present exterior to the firefighter's facemask, a unique alarm pattern is displayed.

Like the FE2005, the FE2006 will transfer a burst of data to the walkie-talkie when the firefighter presses the "talk" button. The FE2006 will also transfer data to the walkie-talkie if the FE2006 receives a "query" command from the walkie-talkie. The data transferred consists of:
A unique serial number identifying the firefighter.
Current environmental temperature
Current body temperature
Current heart-rate
Current breathing rate
Current activity status (mobile or immobile)
Current combustible gas concentration The FE2006 will transmit the following data to a personal computer via infrared beam when the Equipment-Check button is double-clicked:
A unique serial number identifying the Fire-Eye unit.
History of environmental temperature
History of body temperature
History of heart-rate
History of breathing rate
History of activity status
History of combustible gas concentration

FE2007 Basic Unit

Overview . . .

The FE2007 is an infrared camera and heads-up video display system integrated into a firefighter's facemask. In addition to the infrared vision feature, the FE2007 has all the features offered in the FE2006.

Specifications . . .

The FE2007 replaces the facemask lens in existing SCBA facemasks. All materials are strictly compatible with the lens of each equivalent existing facemask.

Like the FE2006, the FE2007 will transfer a burst of data to the walkie-talkie when the firefighter presses the "talk" button. The FE2007 will also transfer data to the walkie-talkie if the FE2007 receives a "query" command from the walkie-talkie. The data transferred consists of:
A unique serial number identifying the firefighter.
Current environmental temperature
Current body temperature
Current heart-rate
Current breathing rate
Current activity status (mobile or immobile)
Current combustible gas concentration The FE2007 will also accept a "query current image" command from the base station operator via the walkie-talkie data link. When that command is received the FE2007 will transfer to the walkie-talkie a block of data corresponding to the current image captured by the infrared camera.

The FE2007 will transmit the following data to a personal computer via infrared beam when the Equipment-Check button is double-clicked:
A unique serial number identifying the Fire-Eye unit.
History of environmental temperature
History of body temperature
History of heart-rate
History of breathing rate
History of activity status
History of combustible gas concentration Although the present disclosure has been described in detail, it should be understood that various changes, substitutions and alterations may be made hereto without departing from the spirit and scope of the disclosure as defined by the claims.

What is claimed is:

1. A system for identifying, monitoring and evaluating environmental and physiological conditions comprising:
    a control unit stored within a housing, the control unit operable to communicate signals associated with environmental and physiological conditions;
    an environmental sensor communicatively coupled to the control unit, the environmental sensor operable to be positioned within an ambient environment and configured to sample the ambient environment at a first rate if an ambient condition is less than a first threshold and to sample at a second rate if the ambient condition is greater than the first threshold, the first rate less than the second rate;
    a physiological sensor communicatively coupled to the control unit, the physiological sensor operable to detect at least one physiological condition of a person wearing the system; and
    an indicator operable to provide an indication to the person representing at least one hazardous or potentially hazardous condition, the indicator further including an optical transmission channel to provide the indication to at least one other person.

2. The system of claim 1 further comprising at least portions of the environmental sensor integrated into and forming a part of a protective facemask, including a first sensor exposed to ambient conditions external to the protective facemask and a second sensor internal to the protective facemask.

3. The system of claim 1 further comprising at least portions of the physiological sensor integrated into and forming a part of a protective facemask.

4. The system of claim 1 further comprising at least portions of the control unit integrated within and forming a part of a protective facemask.

5. The system of claim 1 further comprising at least portions of the indicator integrated into and forming a permanent part of a protective facemask.

6. The system of claim 1 further comprising one or more components of the system integrated into and forming a permanent part of the protective mask.

7. The system of claim 1 further comprising a sensor operable to measure various characteristics of gas mixtures supplied to a person wearing the facemask.

8. The system of claim 1 further comprising a sensor operable to measure nuclear radiation affecting a person wearing the facemask.

9. The system of claim 1 further comprising a biohazard sensor operable to measure the presence of a hazardous biological material affecting the person.

10. The system of claim 1, wherein the person is to program set points for the environmental and physiological conditions.

11. The system of claim 10, wherein the indicator is to provide the indication to the person if at least one of the environmental and physiological conditions is greater than a first set point of the set points.

12. The system of claim 11, wherein the indicator is to provide a second indication to the person if at least one of the environmental and physiological conditions is greater than a second set point of the set points.

13. The system of claim 1, wherein the indicator is to illuminate with a first color for a safe environmental condition and with a second color for an unsafe environmental condition.

14. The system of claim 13, wherein the indicator is to illuminate in a solid manner if the environmental condition is changing in a first direction and to illuminate in a blinking manner if the environmental condition is changing in a second direction.

15. A system for identifying, monitoring, evaluating and alerting a wearer of at least one critical condition comprising:
    a control unit stored within a housing, the control unit operable to communicate signals associated with environmental and physiological conditions;
    an environmental sensor communicatively coupled to the control unit, the environmental sensor operable to be positioned within an ambient environment and configured to sample the ambient environment at a first rate if an ambient condition is less than a first threshold and to sample at a second rate if the ambient condition is greater than the first threshold, the first rate less than the second rate;
    an equipment sensor communicatively coupled to the control unit, the equipment sensor operable to detect and monitor at least one condition of safety equipment associated with a person wearing the system;
    a physiological sensor communicatively coupled to the control unit, the physiological sensor unit operable to detect and monitor at least one physiological condition of the person wearing the system; and
    an indicator operable to provide an indication to the person representing the at least one critical condition, the indicator further including an optical transmission channel to provide the indication to at least one other person.

16. The system of claim 15 further comprising at least one component integrated into an exterior portion of a protective facemask.

17. The system of claim 15 further comprising at least one component integrated into an interior portion of a protective facemask.

18. The system of claim 15 further comprising at least one component integrated into a protective facemask.

19. The system of claim 18 further comprising more than one component integrated into and made a permanent part of a protective facemask.

20. The system of claim 15, wherein the person is to program set points for the environmental and physiological conditions.

21. The system of claim 20, wherein the indicator is to provide the indication to the person if at least one of the environmental and physiological conditions is greater than a first set point of the set points.

22. The system of claim 21, wherein the indicator is to provide a second indication to the person if at least one of the environmental and physiological conditions is greater than a second set point of the set points.

23. The system of claim 15, wherein the indicator is to illuminate with a first color for a safe environmental condition and with a second color for an unsafe environmental condition.

24. A system for identifying, monitoring and evaluating environmental and physiological conditions comprising:
    a control unit stored within a housing, the control unit operable to communicate signals associated with environmental and physiological conditions and to perform a user initiated system check;
    an environmental sensor communicatively coupled to the control unit, the environmental sensor operable to be positioned within an ambient environment and configured to sample the ambient environment at a first rate if an ambient condition is less than a first threshold and to sample at a second rate if the ambient condition is greater than the first threshold, the first rate less than the second rate;
    a physiological sensor communicatively coupled to the control unit, the physiological sensor operable to detect at least one physiological condition of a person wearing the system; and
    an indicator operable to provide an indication to the person representing at least one hazardous or potentially hazardous condition, the indicator further including an optical transmission channel to provide the indication to at least one other person.

25. The system of claim 24, further comprising:
    an equipment sensor communicatively coupled to the control unit; and
    the equipment sensor operable to detect and monitor at least one condition of safety equipment associated with the person wearing the system.

26. The system of claim 24, further comprising the control unit operable to receive and display real time messages from a base station.

27. The system of claim 24, further comprising an operating mode based upon the presence of at least one hazardous or potentially hazardous condition.

28. The system of claim 24 further comprising the environmental sensor removably coupled to safety equipment associated with the person wearing the system.

29. The system of claim 24, further comprising:
    a microprocessor operable to identify, monitor and evaluate the at least one hazardous or potentially hazardous condition; and
    the microprocessor operable to provide a signal to the indicator in response to the at least one hazardous or potentially hazardous condition.

30. The system of claim 24 wherein the physiological sensor comprises a sensor operable to measure the heart rate of the person wearing the system.

31. The system of claim 24 further comprising the indicator operable to display selected environmental and physiological information.

* * * * *